US009877917B2

(12) United States Patent
Cardona Iglesias et al.

(10) Patent No.: US 9,877,917 B2
(45) Date of Patent: Jan. 30, 2018

(54) LIPOSOME FORMULATION SUITABLE FOR TREATING OR PREVENTING TUBERCULOSIS

(75) Inventors: Pere J. Cardona Iglesias, Barcelona (ES); Isabel Amat Riera, Barcelona (ES); Blanca Reyes, Sant Boi de Llobregat (ES); Ariadna Selga, Barcelona (ES); Mercè Amat, Barcelona (ES)

(73) Assignee: ARCHIVEL FARMA, S.L., Badalona (ES)

( * ) Notice: Subject to any disclaimer, the term of this patent is extended or adjusted under 35 U.S.C. 154(b) by 72 days.

(21) Appl. No.: 13/978,001

(22) PCT Filed: Jan. 4, 2012

(86) PCT No.: PCT/EP2012/050080
§ 371 (c)(1),
(2), (4) Date: Jul. 10, 2014

(87) PCT Pub. No.: WO2012/093137
PCT Pub. Date: Jul. 12, 2012

(65) Prior Publication Data
US 2015/0050327 A1 Feb. 19, 2015

(30) Foreign Application Priority Data

Jan. 4, 2011 (EP) .................................. 11150072
Sep. 30, 2011 (EP) .................................. 11183487

(51) Int. Cl.
A61K 39/04 (2006.01)
A61K 39/02 (2006.01)
A61K 39/00 (2006.01)
A61K 9/127 (2006.01)
A61K 31/06 (2006.01)
A61K 47/26 (2006.01)
A61K 45/06 (2006.01)

(52) U.S. Cl.
CPC .............. A61K 9/127 (2013.01); A61K 31/06 (2013.01); A61K 39/04 (2013.01); A61K 45/06 (2013.01); A61K 47/26 (2013.01)

(58) Field of Classification Search
CPC ........ A61K 39/00; A61K 39/02; A61K 39/04; A61K 39/35
See application file for complete search history.

(56) References Cited

U.S. PATENT DOCUMENTS

2003/0022854 A1 1/2003 Dow et al.
2007/0059318 A1 3/2007 Balu-Iyer et al.
2009/0081284 A1 3/2009 Kojima et al.

FOREIGN PATENT DOCUMENTS

| CA | 2453959 A1 | 1/2003 |
| CN | 1874785 A | 12/2006 |
| EP | 1690549 A1 | 8/2006 |
| EP | 2090318 A1 | 8/2009 |
| EP | 2332571 A1 | 6/2011 |
| ES | 2231037 A1 | 5/2005 |
| WO | WO-96/26288 A1 | 1/1999 |
| WO | WO-1999/65465 A1 | 12/1999 |
| WO | WO-2006/117240 A2 | 11/2006 |
| WO | WO-2006/088492 A1 | 2/2008 |
| WO | WO2008127358 A1 | 10/2008 |
| WO | WO-2008/051245 A1 | 5/2009 |
| WO | WO-2009/089535 A2 | 7/2009 |
| WO | WO-2007/109221 A1 | 8/2009 |
| WO | WO-2010/121618 A1 | 10/2010 |
| WO | WO-2012/080369 A1 | 6/2012 |

OTHER PUBLICATIONS

Cardona, P.J. et al., "Immunotherapy with fragmented Mycobacterium tuberculosis cells increases the effectiveness of chemotherapy against a chronical infection in a murine model of tuberculosis", Vaccine, Elsevier Ltd., GB, vol. 23, No. 11, Feb. 3, 2005, pp. 1393-1398.
Mohammed, A.R. et al., "Increased potential of a cationic liposome-based delivery system: Enhancing stability and sustained immunological activity in pre-clinical development", European Journal of Pharmaceutics and Biopharmaceutics, Elsevier Science Publishers B.V., Amsterdam, NL, vol. 76, No. 3, Nov. 1, 2010, pp. 404-412.
Mohammed, A.R., et al., "Lyophilisation and sterilisation of liposomal vaccines to produce stable and sterile products", Methods: A Companion to Methods in Enzymology, Academic Press Inc., New York, NY, US, vol. 40, No. 1, Sep. 1, 2006, pp. 30-38.
Crowe, J.H., et al. "Interactions of Sugars with Membranes", Biochimica et Biophysica ACTA, Elsevier, NL, vol. 947, No. 2, Jun. 9, 1988, pp. 367-384.

(Continued)

Primary Examiner — Rodney P Swartz
(74) Attorney, Agent, or Firm — McCarter & English, LLP; Jill Ann Mello

(57) ABSTRACT

The invention provides liposome formulations comprising fragments from a Mycobacterium tuberculosis-complex strain. It also provides a Mycobacterium tuberculosis-complex strain, fragments of which may be incorporated into selected embodiments of the liposome formulation. The invention further provides suspensions and pharmaceutical compositions comprising the liposome formulations. Furthermore, it discloses the use of the liposome formulations for use in a method of treatment of the human or animal body by therapy, in particular for use in a method of treating or preventing tuberculosis, such as in preventing latent tuberculosis or in tuberculosis prophylaxis, optionally in combination therapy. The formulation of this invention contains sucrose and/or has a lower average particle size than conventional liposome-based agents of tuberculosis therapy, resulting in higher bioavailability and efficiency.

27 Claims, 17 Drawing Sheets

(56) References Cited

OTHER PUBLICATIONS

Zadi, B., et al., "A Novel Method for High-Yield Entrapment of Solutes into Small Liposomes", *Journal of Liposome Research*, Taylor & Francis, Philadelphia, PA, US, vol. 10, No. 1, Feb. 1, 2000, pp. 73-80.

Weinrich Olsen, A., et al., "Protection of mice with a tuberculosis subunit vaccine based on a fusion protein of antigen 85B and ESAT-6", *Infection and Immunity*, American Society for Microbiology, Washington, US, vol. 69, No. 5, May 1, 2001, pp. 2773-2778.

Rosenkrands, Ida, et al., "Cationic liposomes containing mycobacterial lipids: a new powerful Th1 adjuvant system", *Infection and Immunity*, American Society for Microbiology, Washington, US, vol. 73, No. 9, Sep. 1, 2005, pp. 5817-5826.

Zumbuehl, O., et al., "Liposomes of controllable size in the range of 40 to 180 nm by defined dialysis of lipid/detergent mixed micelles", *Biochimica et Biophysica Acta. Biomembranes*, Amsterdam, NL., vol. 540, No. 1, Jan. 8, 1981, pp. 252-262.

Orme, et al., "Preclinical testing of new vaccines for tuberculosis: A comprehensive review", *Vaccine*, Elsevier Ltd., GB, vol. 24, No. 1, Jan. 9, 2006, pp. 2-19.

International Search Report for PCT/EP2012/050080, dated Mar. 2, 2013.

Extended European Search Report for EP 11150072, dated May 31, 2011.

Mir F. A., et al., A Multicistronic DNA VAccine Induces Significant Protection Against Tuberculois in Mice and Offers Flexibility in the Expressed Antigen Repertoire, *Clinical and Vaccine Immunology*, 2009, 16(10):1467-1475.

Szoka Jr., F. et al., Procedure for preparation of liposomes with large internal aqueous space and high capture by reverse-phase evaporation, *Proc. Natl. Acad. Sci. USA*, 1978, 75(9):4194-4198.

Deng Y et al., "The antiasthma effect of neonatal BCG vaccination does not depend on the Th17/Th1 but IL-17/IFN-γ balance in a BALB/c mouse asthma model". *J. Clin. Immunol.* Jun. 2011;31(3):419-29.

International Search Report & Written Opinion issued in PCT/IB2012/000353, dated Aug. 14, 2012.

Obihara CC et al., "*Mycobacterium tuberculosis* infection may protect against allergy in a tuberculosis endemic area". *Clin. Exp. Allergy* Jan. 2006;36(1):70-6.

Riffo-Vasquez Y et al., "Effect of *Mycobacterium tuberculosis* chaperonins on bronchial eosinophilia and hyper-responsiveness in a murine model of allergic inflammation". *Clin. Exp. Allergy* May 2004;34(5):712-9.

Strauss, G. et al., "Stabilization of lipid bilayer vesicles by sucrose during freezing", *Proc. Natl. Acad. Sci. USA*, Apr. 1986, vol. 83, pp. 2422-2426.

Zhang, Jing and Run-guang Sun, "Liquid Crystalline Structure and Stability of Liposomes Studied by Atomic Force Microscope", *Chinese Journal of Liquid Cyrstals and Displays*, vol. 18, No. 4, pp. 266-270, Aug. 2003.

Zhang GS et al., "New insights into the effects of *Mycobacterium bovis* Bacillus Calmette-Guerin on asthma". *Chin. Med. J.* (Engl). Mar. 5, 2009;122(5):577-83.

Lemmer, Y. et al., "Detection of Antimycolic Acid Antiboidies by Liposomal Biosensors," *Methods in Enzymology* (2009), 464: 79-104 (209).

Arnoldussen, D.L, et al., "BCG vaccination and allergy: A systematic review and meta-analysis", *J. Allergy Clin. Immunol.*, vol. 127, No. 1, 246-253, 2011.

Jentoft, H.F. et al., "Absence of relationship between tuberculin reactivity and asthmatic symptoms, level of $FEV_1$ and bronchial hyperresponsiveness in BCG vaccinated young adults," *Allergy*, vol. 57, pp. 336-340, 2002.

Youmans, A.S. et al., "Effect of mitochondrial stabilizers on the immunogenicity of the particulate fraction isolated from mycobacterium tuberculosis", *Journal of Bacteriology*, vol. 87, No. 6, pp. 1346-1354, 1964.

Yadava, P., et al., "Effect of Lyophilization and Freeze-thawing on the Stability of siRNA-Liposome Complexes", *AAPS PharmSciTech*, vol. 9, No. 2, Jun. 2008, pp. 335-341.

LIPOSOME FORMULATION SUITABLE FOR TREATING OR PREVENTING TUBERCULOSIS

RELATED APPLICATIONS

This application is a 35 U.S.C. §371 national stage filing of International Application No. PCT/EP2012/050080, filed Jan. 4, 2012, which claims the benefit of European Patent Application No. 11150072.4, filed Jan. 4, 2011 and European Patent Application No. 11183487.5, filed Sep. 30, 2011. The entire contents of each of these applications are explicitly incorporated herein by reference.

INTRODUCTION AND BACKGROUND ART

Field of the Invention

The present invention provides liposome formulations comprising fragments from a *Mycobacterium tuberculosis*-complex strain, as well as suspensions and pharmaceutical compositions comprising these formulations and their respective use in a method of treatment, particularly for treating or preventing tuberculosis. The formulation of this invention contains sucrose and/or has a lower average particle size than conventional liposome-based agents of tuberculosis therapy, resulting in higher bioavailability and efficiency.

Background Art

Tuberculosis is a chronic infectious disease caused by the *Mycobacterium tuberculosis*-complex (MTB-C) bacilli, which includes the *Mycobacterium* species *M. tuberculosis, M. bovis, M. microti* and *M. africanum*. The main distinctive feature of the mycobacterial cellular envelope is the thick and waxy cell wall. The properties of the cell wall barrier also contribute to the intracellular survival of the organism by acting as a direct modulator in the immunological reactions between the host and MTB-C bacilli. The envelope consists of two distinct parts, the plasma membrane and, around it, the wall. The cell wall is a skeleton formed by a covalently linked structure of peptidoglycan, with a branched-chain polysaccharide, the arabinogalactan, attached by phosphodiester bonds. The arabinogalactan distal ends are esterified with high-molecular weight fatty acids, the mycolic acids, of sizes and structures unique to mycobacteria.

According to the World Health Organization, 9,000,000 new cases of people manifesting the disease are recorded worldwide every year and about 2,000,000 people die. It is considered that there are more than 2,700,000,000 infected people worldwide and that 90-100 million more new infections are generated each year.

Various vaccines against tuberculosis based on cell wall fragments of virulent or avirulent strains of *Mycobacterium* are described in the state of the art. The vaccine which is currently used in the preventive treatment against tuberculosis is based on bacteria of the strain called BCG (Bacillus Calmette-Guerin), an attenuated variant of *M. bovis*. It is also known that the adjuvant used in the composition of the vaccine can greatly influence the effectiveness thereof.

Trehalose mycolates, particularly trehalose dimycolate, are the most bioactive lipids in *M. tuberculosis* extracts, inducing a proinflammatory cascade that influences granuloma formation. It should be noted that no bibliographic data exist on the amount of these compounds present in the cell wall of *M. tuberculosis*. Any sample derived of this species has a high biological complexity. Therefore, to perform quantitative analysis, aggressive, complex and long purification steps would be required, resulting in too low amounts of the purified compound to perform further structural analyses. This is the reason why no published data exist about the exact percent of each compound in the cell wall of *M. tuberculosis*. Several glycolipids are typical constituents of MTB-C cells, such as liporabinomannan. Lipoarabinomannan is associated with MTB-C virulence.

E. Ribi et al., Nature 1963, 198, pages 1214 to 1215, describe the immunization assays performed with a composition comprising cell wall fragments of the avirulent Bacillus Calmette Guerin (BCG) strain and mineral oil. Said fragments are obtained by homogenisation of a culture of said strain in mineral oil. The composition is more effective than the conventional vaccine (BCG). Nevertheless, it is described in the same article that the cell wall fragments do not induce any immunological response when they are obtained by homogenisation in water and in the absence of the mineral oil.

D. P. Pal et al., Indian J. Med. Res. 1977, 65, pages 340 to 345, describe a vaccine prepared with cell wall fragments of the virulent H37Rv strain and mineral oil. In this case the cell wall fragments are obtained by means of homogenisation of the dead cells in aqueous phase, and the mineral oil is subsequently added to the composition. It is also described that the cell wall fragments homogenised in aqueous phase are not immunogenic and that the presence of mineral oil is necessary for the vaccine to be effective.

G. K. Khuller et al., Folia Microbiol., 1992, 37, pages 407 to 412, describe the protective efficacy of different fractions of the cell wall of the avirulent H37Ra strain of *M. tuberculosis* formulated with Freund's incomplete adjuvant, which also includes mineral oil.

E. M. Agger et al., Scand. J. Immunol., 2002, 56, pages 443 to 447, describe vaccines comprising cell wall fragments of the virulent H37Rv strain, which are effective when they include the cationic surfactant dimethyldioctadecylammonium bromide as an adjuvant. It is also described that the assays conducted with homogenised *M. tuberculosis* bacilli which do not contain the mentioned adjuvant do not generate levels of resistance against tuberculosis in the mouse model.

I. M. Orme Vaccine, 2006, 24, pages 2 to 19, which is a review article of vaccines against tuberculosis, describes that the conventional Bacillus Calmette-Guerin (BCG) based vaccine is essentially ineffective in protecting adult people against tuberculosis.

Individuals who may benefit from a treatment or prophylaxis related to tuberculosis can be grouped in the following four sub-groups:

(I) Individuals who are not exposed to the disease. Prophylactic vaccination can prevent infection of such individual.

(II) Individuals who are exposed to the disease but not yet infected. The skin tuberculin test (TST) is negative. Primary prophylaxis can prevent infection of such individuals.

(III) Individuals with latent tuberculosis who are not ill. The risk of the outbreak of the disease can be lowered by applying chemotherapy. The chemotherapy also provides the advantage that these individuals basically cease being high risk sources of the infection.

(IV) Individuals who are ill, i.e. suffering from the disease, normally with primary forms of the disease, but little or not contagious. Chemotherapy prevents these individuals from becoming contagious.

Once the infection has started, the state of the art describes various treatments for defending the development of active tuberculosis in infected individuals, i.e. individuals with latent tuberculosis.

For example, in the patent application EP2196473 A1, it is described that, for treating tuberculosis in infected individuals, those who have not yet developed the disease as well as those who have already developed the disease, various drugs, including isoniazide, can be administered for a time extending for several months.

In the patent application ES 2231037 A1 the use of an immunotherapeutic agent is described that comprises cell fragments of a virulent strain of *Mycobacterium tuberculosis*-complex (MTB-C) for the preparation of a medicament for treatment of tuberculosis in infected individuals in combination with other drugs, like isoniazide or rifampicin. This patent application also discloses a method for the preparation of an immunotherapeutic agent comprising cell wall fragments of a strain of MTB-C.

As outlined in WO 2010/031883 A1, the transmission of the latent tuberculosis infection occurs mainly through breathing aerosols infected with *M. tuberculosis*. Therefore, persons in direct contact with patients suffering pulmonary tuberculosis, and thus that are able to disseminate infected aerosols, such as persons who live together or have any other type of intense or frequent contact with them, are considered a risk group.

Currently, the primary prophylaxis of the infection that is administered normally to group I individuals (as above) is a primary chemoprophylaxis based on daily administration of isoniazide in a dose of 5 mg/kg without exceeding 300 mg/day. This treatment is indicated in all individuals of any age who are TST negative, who live together and/or have any other type of close contact with infected individuals. In this case, the chemoprophylaxis needs to be maintained for three months after having ceased the contact with the infectious source or after the source has ceased being infective. However, chemoprophylaxis can in some cases lead to secondary unwanted effects, as described by Martínez et al., Arch. Bronchoneumol., 2005, 41(1), pages 27-33.

Medications comprising fragments of a virulent *M. tuberculosis*-complex (MTB-C) strain have been described for example in EP1690549 B1, EP2090318 A1 and PCT/ES2009/000436. EP2090318 A1 and PCT/ES2009/000436 disclose pharmaceutical compositions comprising fragments of a virulent *M. tuberculosis*-complex (MTB-C) strain for the use as a medicament suitable for prophylactic prevention of tuberculosis, optionally in combination with other drugs. On the other hand, EP1690549 B1 discloses pharmaceutical compositions suitable for the treatment of tuberculosis, comprising MTB-C fragments, optionally in combination with other drugs.

It has been reported in the patent application EP 2090318 A1 that the administration of a drug comprising an agent based on cell wall fragments of a virulent strain of MTB-C is able to induce a Th1 type interferon-γ generating response against *M. tuberculosis*-specific antigens. Said antigens include Ag85B and Ag85A, which are part of the complex Ag85, consisting of a family of low molecular weight proteins playing a decisive role in the biosynthesis of the cell wall and produced in considerable amounts when the bacterial cultivation is in the logarithmic growth (log) phase. It has further been reported in EP 2090318 A1 that the conventional Bacillus Calmette-Guerin (BCG) based vaccine does not generate an immunoprotective response against antigens of complex Ag85. The production of interferon-γ by the specific lymphocytes has a key role: It enables the infected macrophages to stop the growth of the bacilli (North & Young, Ann. Rev. Immunol., 2004, 22:599-623).

The World health Organization has recognized that the risk of developing tuberculosis (TB) is estimated to be between 20-37 times greater in people living with HIV than among those without HIV infection. An overview is given in "Guidelines for intensified tuberculosis case-finding and isoniazid preventive therapy for people living with HIV in resource-constrained settings" WHO Guidelines 2011, ISBN: 978 92 4 150070 8). However, the isoniazid preventive therapy is not a vaccination that would provide long-lasting protection to HIV positive individuals. Rather, the isoniazid needs to be administered regularly, and isoniazid resistance corroborates this therapy. Thus, there remains a need of providing more powerful preventive and therapeutic treatments for HIV positive human subjects.

OBJECT OF THE INVENTION

The object of the present invention is the provision of an improved agent suitable for preventing or treating tuberculosis, such as in prophylaxis of latent tuberculosis, primary prophylaxis, and/or treatment of latent or active tuberculosis, in both HIV positive and HIV negative human subjects. A further object is as the provision of a MTB-C strain suitable for the preparation of the agent. The process for preparing the agent is a further an object of this invention.

Definitions

"FCMtb" stands for fragments from a *Mycobacterium tuberculosis*-complex (MTB-C) strain "particle size" refers to, if not otherwise specified, the diameter of the particles. Where the particle size can not be determined exactly, the approximate particle size is meant.

"z-average" is the average particle size, determinable as described in the material and methods section.

Abbreviations

AIDS Acquired immunodeficiency syndrome
BCG Bacillus Calmette-Guérin
CFU Colony-forming unit
DP Drug product
DS Drug substance
ELISA Enzyme-linked immunosorbent assay
ELISPOT Enzyme-linked immunospot assay
EMEA European Medicines Agency
FCMtb Fragments of *M. tuberculosis* cells
FIM First in man
HIV human immunodeficiency virus
IFN-γ Interferon gamma
IGTIP Institut per a la Recerca en Ciènces de la Salut Germans Trias i Pujol
IMP Investigational medicinal product
IPC In process controls
LCS Liposome concentrate suspension
LTBI Latent tuberculosis infection
LPS Lipopolysaccharide
Mtb *Mycobacterium tuberculosis*
Mtb *Mycobacterium tuberculosis*-complex
NZB New Zealand Black
NZW New Zealand White
PPD Protein-purified derivative
q.s. Quantum sufficit
TB Tuberculosis
TST Tuberculosis skin test
WHO World Health Organization
w/v weight/volume
w/w weight/weight

SUMMARY OF THE INVENTION

The invention provides liposome formulations comprising fragments from a *Mycobacterium tuberculosis*-complex (MTB-C) strain (FCMtb) and a liposome forming agent.

In a particular embodiment, the z-average size of the particles, as determinable for example by dynamic light scattering, is 120 nm or less, preferably 110 nm or less, more preferably 95 nm or less, and most preferably 80 nm or less. In an alternative embodiment the liposome formulation comprises 1 to 20% (w/v) sucrose, preferably 2 to 12% (w/v) sucrose, more preferably 3 to 8% (w/v) sucrose, and most preferably 4 to 6% (w/v) sucrose. It is important to note that, while each of these two embodiments may be fulfilled individually, these embodiments are not to be seen as mutually exclusive and may well occur in combination.

In one particular embodiment the above-described liposome formulation has a z-average particle size in the range from 40 to 120 nm, preferably from 50 to 110 nm, more preferably from 55 to 95 nm, and most preferably from 55 to 80 nm.

In an alternative particular embodiment the average particle size of the above-described liposome formulation may be smaller, so that the liposome formulation is an emulsion, i.e. in this particular embodiment the z-average size of the particles is preferably below 40 nm.

In a preferred embodiment of any one or more of the above-described embodiments, the liposome formulation is a liposome formulation, wherein the polydispersity index of the particles is 0.4 or less, preferably 0.3 or less.

In a more preferred embodiment of any of the above-described embodiments, the *Mycobacterium tuberculosis*-complex (MTB-C) strain is a virulent *Mycobacterium tuberculosis*-complex (MTB-C) strain.

It is further preferred that in any of the embodiments described above, the ratio of (a): the fragments from a *Mycobacterium tuberculosis*-complex (MTB-C) strain and (b) the liposome forming agent, is between 0.01:1 and 1:1, preferably between 0.06:1 and 0.1:1.

In a more preferred embodiment of any of the above-described, the liposome formulation additionally comprises: (d) a tensioactive agent. In an even more preferred embodiment, the liposome formulation comprising (d) the tensioactive agent, is a liposome formulation, wherein the ratio between (a) and (d) is between 0.1:1 and 10:1 (w/w), preferably 0.5:1 and 2:1 (w/w), and most preferably between 0.6:1 and 0.8:1 (w/w).

In a particular embodiment of the above-described, the liposome forming agent of the liposome formulation is a phospholipid, preferably lecithin, more preferably one selected from the group consisting of egg lecithin or soy lecithin, and most preferably soy lecithin, each of which may be hydrogenated, partially hydrogenated or non-hydrogenated.

In a preferred embodiment of the surfactant-containing liposome formulation, the tensioactive agent is selected from cholate, deoxycholate, cholesterol and cholesterol hemisuccinate.

In a more preferred embodiment, the liposome formulation described above is a liposome formulation, wherein the fragments of MTB-C cells are or comprise cell wall fragments.

In another more preferred embodiment, the liposome formulation described above comprises fragments of the MTB-C strain NCTC 13536, which was deposited in 2010 at the NCTC in London. This strain is synonymously called 511, so that the names NCTC 13536 and 511 can be used interchangeably.

In an even more preferred embodiment, the liposome formulation described above comprises at least two, preferably three, more preferably four, most preferably all of the following:
  (i) a first polypeptide having a molecular weight of about 70 kDa, similar to a mass fingerprint of *M. tuberculosis* HSP70 protein (Rv0350),
  (ii) a second polypeptide having a molecular weight of about 38 kDa, similar to a mass fingerprint of *M. tuberculosis* 38 kDa protein (Rv 0934),
  (iii) a third polypeptide having a molecular weight of about 30 kDa, similar to a mass fingerprint of *M. tuberculosis* Ag85B protein (Rv 1866c), and
  (iv) a fourth polypeptide having a molecular weight of about 10 kDa, similar to a mass fingerprint of *M. tuberculosis* CFP10 protein (Rv3874), and
  (v) a fifth polypeptide having a molecular weight of about 6 kDa, similar to a mass fingerprint of *M. tuberculosis* ESAT-6 protein (Rv3875).

In a yet more preferred embodiment, the liposome formulation comprises a lipopolypeptide having a molecular weight of about 19 kDa, similar to a mass fingerprint of *M. tuberculosis* 19 kDa lipoprotein antigen precursor LpqH (Rv 3763).

Even more preferably, the liposome formulation described above is further characterized in that at least one of the following antigens of *Mycobacterium tuberculosis*, or fragment thereof, is present: HSP70, 38 kDa protein and Ag85B. Fragment in this sense is any part, such as for example a degradation product, of any of these polypeptides.

In a more preferred embodiment, the liposome formulation described above contains lipids which are typically found in *Mycobacterium tuberculosis* or derivatives thereof, such as conjugation products like sugar conjugated lipids. It is further preferred that one or more of mycolic acids, preferably belonging to any one or more of types I, III or IV, is comprised. Alternatively or in addition, a sugar-conjugated mycolate, preferably trehalose dimycolate may be comprised in the formulation. Alternatively or in addition, it is further preferred, that at least one MTB-C-derived glycolipid is present in the liposome formulation according to the present invention, and a preferred glycolipid is liporabinomannan.

The liposome formulation described above may additionally comprise one or more surfactants, which is/are preferably from the group of non-ionic surfactants.

In a further preferred embodiment the liposome formulation according to any of the preceding claims additionally comprises one or more salts or solution thereof, whereby the preferred salt is sodium chloride.

In an even more preferred embodiment of any of the above the liposome formulation of this invention is freeze-dried.

The invention also provides a suspension, wherein the liposome formulation of any of the preceding claims is reconstituted in a solvent. In a preferred embodiment, the solvent of this suspension is aqueous, and preferably is or comprises physiological serum.

The invention also provides a pharmaceutical composition comprising the liposome formulation as described in any one or more of the embodiments above, or the suspension as described in any one or more of the embodiments described above, and a pharmaceutically acceptable carrier or diluent or excipient, whereby any substance suitable as carrier, diluent or excipient may be used. In a preferred embodiment thereof, this pharmaceutical composition additionally comprises a pharmaceutically acceptable adjuvant.

The invention also provides a product for use in a method of treatment of the human or animal body by therapy. That is, it provides the liposome formulation according to any one or more of the embodiments described above, the suspension according to any one or more of the embodiments described above, or the pharmaceutical composition according to any one or more of the embodiments described above, for use in a method of treatment of the human or animal body by therapy. In a particular embodiment, the invention provides this liposome formulation, suspension or pharmaceutical composition for injection. In another particular embodiment, the invention provides this liposome formulation, suspension or pharmaceutical composition for use in a method of treating or preventing tuberculosis. These particular embodiments may be met individually or in combination.

In a more particular embodiment, the invention provides the liposome formulation, suspension or pharmaceutical composition according to what is described above in relation to the use thereof in a method of treatment of the human body by therapy, further characterized in that it is for administration to the human body in a dose comprising 1 to 1000, preferably 3 to 250, more preferably 4 to 80, and most preferably about 5, about 25 or about 50 μg/dose FCMtb.

In three more particular embodiments (a) to (c), the liposome formulation, suspension or pharmaceutical composition according to what is described above in relation to the use thereof in a method of treatment of the human or animal body by therapy is (a) for use in a method of prevention of active tuberculosis in individuals with a latent tuberculosis infection, (b) for use in a method of primary prophylaxis of tuberculosis in order to prevent infection of individuals who had been exposed to the disease, but are not yet infected, or (c) for use in a method of treating or preventing latent tuberculosis.

In a preferred embodiment of the above liposome formulation, suspension or pharmaceutical composition for the use thereof in a method of treatment of the human or animal body by therapy is its use in combination therapy or adjunctive therapy. Adjunctive therapy is an additional or secondary therapy combined with a primary treatment that increases effectiveness in treating a condition. A particular embodiment of combination therapy is one wherein the combination therapy comprises an antibiotic, preferably one or more of isoniazide and an ansamycine, whereby the ansamycine is most preferably rifampicin. In a particular embodiment of the present invention, adjunctive therapy is administered to a HIV positive human subject, and a single dose of 25 μg FCMtb is preferred.

The invention also provides a process for preparing any of the agents, that is the liposome formulation, the suspension or the pharmaceutical composition.

The invention further provides the MTB-C strain NCTC 13536, deposited in 2010 at the NCTC in London.

DETAILED DESCRIPTION OF THE INVENTION

The invention provides liposome formulations comprising fragments from a *Mycobacterium tuberculosis*-complex (MTB-C) strain (FCMtb) and a liposome forming agent.

Unless expressly specified otherwise, the term "comprising" is used in the context of the present application to indicate that further members may optionally be present in addition to the members of the list introduced by "comprising". It is, however, contemplated as a specific embodiment of the present invention that the term "comprising" encompasses the possibility of no further members being present, i.e. for the purpose of this embodiment "comprising" is to be understood as having the meaning of "consisting of".

The detailed description discloses specific and/or preferred variants of the individual features of the invention. The present invention also contemplates as particularly preferred embodiments those embodiments, which are generated by combining two or more of the specific and/or preferred variants described for two or more of the features of the present invention.

It is generally accepted that a liposomation process generates a lipidic environment, facilitating the solubility and leading to a suspension of substances, such FCMtb. Liposomes within the meaning of this invention may be unilamellar, multilammellar or combinations thereof.

FCMtb can be of any type of substance derived from the MTB-C strain, whereby fragments derived from proteins and/or lipids are preferred. FCMtb within the sense of this application is typically a mixture of different protein antigens and lipids from MTB-C cells. The cell fragments may be obtained by any method known to the person skilled in the art suitable for fragmenting microbial or bacterial cells, such as specifically MTB-C cells, for example homogenisation. The homogenisation can be carried out by means of ultrasound sonication, or by means of the use of small beads of approximately 0.1 mm in diameter, for example, silica or zirconia/silica beads, together with a mechanical homogenizer. A mechanical homogenizer that can be used, for example, is the BioSpec BeadBeater® model. The MTB-C cells are broken by means of this homogenisation process, so that small cell fragments, typically including small cell wall fragments, are obtained. A typically relevant feature of the manufacturing of the cell fragments is the "detoxification" of the cell wall fragments by delipidation, well known to the person skilled in the art, a process that allows removing the endotoxin-like molecules. The FCMtb is therefore preferably detoxified and pasteurized, the obtained liposome formulation is then sterile and free of endotoxins. The dispersion of cell fragments in buffer can optionally be lyophilised to facilitate the storage thereof. To that end, the dispersion can be distributed into vials and lyophilised at a temperature between −15° C. and −120° C., such as for example −45° C. and with a vacuum, such as between 0.1 and 0.5 mbar.

The liposomes according to this invention usually have a size distribution in which at least 99.9% (by number) are smaller than 1 μm. In a particular embodiment, the z-average size of the particles, as determinable by dynamic light scattering, is 120 nm or less, preferably 110 nm or less, more preferably 95 nm or less, and most preferably 80 nm or less. In dynamic light scattering the z-average parameter is considered a stable and important number obtainable by the technique, and the size number that is preferably used for quality control purposes. Preferably, the liposomes of the formulation according to this invention are monomodal, i.e. they show only one peak in dynamic light scattering measurements. More preferably, the liposomes of the formulation according to this invention are spherical, as can be tested by electron microscopy of freeze-fracturing preparations of the liposome formulation, as shown in Example 9. Spherical thereby means that for at least 90% of the liposome particles (by number), all surface points of the individual particle have similar or identical distance to the center of the liposome, i.e. the minimal radius of such a particle relates to the maximal radius of the same particle in a ration of 0.6 or more, 0.7 or more, 0.8 or more or 0.9 or more. The liposome formulation according to the present invention can comprise multilamellar or unilamellar liposomes, or a mixture thereof. In line with standard knowledge of the person skilled in the art, the dynamic light scattering measurements should be performed in a suitable buffer, i.e. a buffer which does not by itself cause disruption, disintegration or fusion of the liposomes or significantly destabilize them physically in any other way. As a rule of thumb, any buffer may be suitable as long as both ionic strength and pH value are comparable to the buffer in which the liposomes had been formed may be suitable. Preferably, a buffer of similar or identical composition to the buffer in which the liposomes had been formed, is used.

In an alternative embodiment, the liposome formulation additionally comprises 1 to 20% (w/v) sucrose, preferably 2 to 12% (w/v) sucrose, more preferably 3 to 8% (w/v) sucrose, and most preferably 4 to 6% (w/v) sucrose. Approximately 5% sucrose is particularly preferred.

It is important to note that, while each of these embodiments relating, the one relating to a particular particle size and the other relating to the presence of sucrose, may be fulfilled individually, these embodiments are not to be seen as mutually exclusive and may well occur in combination.

In one particular embodiment, the above-described liposome formulation has a z-average particle size in the range from 40 to 120 nm, preferably from 50 to 100 nm, and more preferably from 55 to 95 nm, and more preferably from 55 to 80 nm. The z-average particle size is thereby preferably measured by dynamic light scattering, as described in general above and in detail in the section "Materials and methods"

In an alternative particular embodiment, the z-average particle size of the above-described liposome formulation may be smaller, so that the liposome formulation is an emulsion, i.e. in this particular embodiment the z-average size of the particles is preferably below 40 nm.

In a preferred embodiment of any one or more of the above-described embodiments, the liposomes of the formulation according to this invention are furthermore monodisperse, which means that no significant width of the size distribution is observed. This is technically tested by a low polydispersity index (PDI) as determined by dynamic light scattering, such as 0.4 or less, preferably 0.3 or less, Hence, the liposome formulation is a liposome formulation, wherein the polydispersity index of the particles as determinable by dynamic light scattering is 0.4 or less, preferably 0.3 or less, and most preferably 0.25 or less.

The fragments from the *Mycobacterium tuberculosis*-complex (MTB-C) strain are obtainable by a process comprising an upstream process and a downstream process. For illustrative purposes, the five main steps are briefly described here and particular modes of carrying out the process are given in Examples 2 and 3 below.

Upstream process (Example 2):
Step 1: Culture of *Mycobacterium tuberculosis*
Step 2: Harvest of *Mycobacterium tuberculosis* and freezing of crude extract
Downstream process (Example 3):
Step 3: Cell fragmentation and delipidation
Step 4: Pasteurization
Step 5: Freeze-drying (optional)

In a more preferred embodiment of any of the above-described embodiments, the *Mycobacterium tuberculosis*-complex (MTB-C) strain is a virulent *Mycobacterium tuberculosis*-complex (MTB-C) strain. Virulent refers to the pathogenecity by case and/or the ability of the bacilli to invade the tissues of the host. The virulent strain can be any virulent strain of any of the species belonging to MTB-C, but a strain belonging to *M. tuberculosis* is preferred. The MTB-C strain according to this invention may be cultivated by inoculation in culture media well-known by the person skilled in the art, for example Middlebrook 7H10 or 7H11 agar, Sauton's medium or Proskauer-Beck medium. The culture of the virulent strain is preferably performed over an extended time period, such as, for example, a period equal to or greater than three weeks, preferably comprised between 3 and 4 weeks. The temperature of the culture is preferably maintained between 34° C. and 38° C. Once the culture ends, the cells are harvested and isolated using techniques well known in the art, such as those described in patent application ES2231037-A1.

The liposome agent of the liposome formulation is preferably a hydrogenated, partially hydrogenated or non-hydrogenated phospholipid. The phospholipid used can be or comprise, for example: phosphatidylcholine, phosphatidylserine and phosphatidyl-inositol. Most typical is phosphatidylcholine, which can be synthesized or isolated from a variety of natural sources. Preferably the liposome forming agent is or comprises lecithin, selected from the group consisting of egg lecithin and soy lecithin. Soy lecithin is a complex mixture of phospholipids including inter alia phosphatidylcholine, and is particularly preferred. Typical lipids which may also be comprised in the formulation, either as liposome forming agent itself, or as further component, are: dicetyl phosphate (DCP), dimyristoyl phosphatidylcholine (DMPC), dimyristoyl phosphatidylglycerol (DMPG), dioleoyl phosphatidylcholine (DOPc), dioleoyl phosphatidylethanolamine (DOPE), dioleoyl phosphatidylserine (DOPS), dipalmitoyl phosphatidylcholine (DPPC), dipalmitoyl phosphatidylglycerol (DPPG), phosphatidylcholine (PC) and/or phosphatidylserine (PS), whereby the respective lipid may be hydrogenated, partially hydrogenated or non-hydrogenated. The liposomes can be formed using conventional auxiliary lipids and techniques well-known by the person skilled in the art, such as those described in the patent application ES2231037-A1.

It is further preferred that in any of the embodiments described above, the ratio of (a): the fragments from a *Mycobacterium tuberculosis*-complex (MTB-C) strain and (b) the liposome forming agent, is between 0.01:1 and 1:1, preferably between 0.06:1 and 0.1:1. In a more preferred embodiment of any of the above-described, the liposome formulation additionally comprises: (d) a tensioactive agent. Generally, all types of agents capable of changing the value of surface tension may be used as tensioactive agent in the sense of this invention, but excluded are compounds which fall under the definition of the liposome-forming agent given above. Various types of tensioactive agents are known to the person skilled in the art and may be used in the liposome formulation according to the present invention. As is known to the skilled person, tensioactive agents are generally chemicals with a polar-nonpolar structure. Without wishing to be limited to any particular theory, tensioactive agents generally have the tendency to locate to the surface of particles, thereby creating a monomolecular layer on the interface that reduces the surface tension value. Tensioactive agents are also referred to as surfactants or active surface agents. In a preferred embodiment of the surfactant-containing liposome formulation, the tensioactive agent is selected from sterols and derivatives thereof, such as cholesterol, and/or bile salts or derivatives thereof, such as cholate. Particularly preferred embodiments are those wherein the tensioactive agent is selected from cholate, deoxycholate, cholesterol and cholesterol hemisuccinate. A good, but not limiting mode of carrying out the invention is where the liposomes of the formulation comprise both soy-derived lecithin and sodium cholate.

In an even more preferred embodiment, the liposome formulation comprising (d) the tensioactive agent, is a liposome formulation, wherein the ratio between (a) and (d) is between 0.05:1 and 3:5 (w/w). Various types of liposome forming agents may be used, as are well known to the person skilled in the art.

The liposomes can optionally contain additives improving their stability, for example: vitamin E, which is believed to act as a lipid antioxidant.

In a more preferred embodiment, the liposome formulation described above is a liposome formulation, wherein the fragments of MTB-C cells are or comprise cell wall fragments.

Any strain belonging to MTBC, and preferably any strain belonging to *Mycobacterium tuberculosis*, may be used. In another more preferred embodiment, the liposome formulation described above comprises fragments of the MTB-C strain NCTC 13536, which was deposited in 2010 at the NCTC in London (Example 1). Another strain which may be used, and fragments of which may therefore be comprised in the liposome formulation, is called H37Rv, which, for example, can be obtained from the National Collection of Type Cultures (NCTC), London, Great Britain (deposit number NC007416) and is often used by researchers in this field. It is also possible that more than one strain be used, i.e. that the liposome formulation comprises fragments of various, such as two, three, or more than three strains.

Considering the approximately 4000 putative antigens of *M. tuberculosis*, it is impossible to analyse drug substance for all of these proteins. Nevertheless, certain MTB-C proteins have been shown to be relevant for the desired immune response. These are five protein bands have approximate sizes of 6, 10, 30, 38, and 70 kDa (Renshaw, et al., 2005, *EMBO Journal* 24, 2491-2498; Singh, et al., 2005, *Clin. Diagn. Lab. Immunol.* 12(2), 354-358). Therefore, in an even more preferred embodiment, the liposome formulation described above comprises at least two, preferably three, more preferably four, and most preferably all of the following:

(i) a first polypeptide having a molecular weight of about 70 kDa as measured following electrophoresis on a sodium dodecylsulfate (SDS) polyacrylamide gel, wherein the first polypeptide has a mass fingerprint similar to a mass fingerprint of *M. tuberculosis* HSP70 protein (Rv0350), (ii) a second polypeptide having a molecular weight of about 38 kDa as measured following electrophoresis on a sodium dodecylsulfate (SDS) polyacrylamide gel, wherein the second polypeptide has a mass fingerprint similar to a mass fingerprint of *M. tuberculosis* 38 kDa protein (Rv 0934), (iii) a third polypeptide having a molecular weight of about 30 kDa as measured following electrophoresis on a sodium dodecylsulfate (SDS) polyacrylamide gel, wherein the third polypeptide has a mass fingerprint similar to a mass fingerprint of *M. tuberculosis* Ag85B protein (Rv 1866c), and (iv) a fourth polypeptide having a molecular weight of about 10 kDa as measured following electrophoresis on a sodium dodecylsulfate (SDS) polyacrylamide gel, wherein the fourth polypeptide has a mass fingerprint similar to a mass fingerprint of *M. tuberculosis* CFP10 protein (Rv3874), and (v) a fifth polypeptide having a molecular weight of about 6 kDa as measured following electrophoresis on a sodium dodecylsulfate (SDS) polyacrylamide gel, wherein the fifth polypeptide has a mass fingerprint similar to a mass fingerprint of *M. tuberculosis* ESAT-6 protein (Rv3875).

In a yet more preferred embodiment thereof, the liposome formulation further comprises a lipopolypeptide having a molecular weight of about 19 kDa as measured following electrophoresis on a sodium dodecylsulfate (SDS) polyacrylamide gel, wherein the lipopolypeptide has a mass fingerprint similar to a mass fingerprint of *M. tuberculosis* 19 kDa lipoprotein antigen precursor LpqH (Rv 3763). The respective band can be visualized by methods known in the art, such as silver staining. The researchers of the present invention surprisingly found that this polypeptide induces a high total IgG humoral response, which may be the highest humoral response among all antigens in the formulation.

Examples of how the polypeptides or lipopolypeptides may be identified are given in Example 4.

Even more preferably, the liposome formulation described above is further characterized in that at least one of the following antigens of *Mycobacterium tuberculosis*, or fragment thereof, is present: HSP70, 38 kDa protein, Ag85B, and most preferably at least one of HSP70, 38 kDa protein and Ag85B. Fragment in this sense is any part, such as for example a degradation product, of any of these polypeptides. Various ways of obtaining such fragments are possible, for example chemical or enzymatic hydrolysis, whereby it is not relevant if the fragmentation had occurred purposely or not, prior to liposome formation or thereafter. It is preferred that the respective fragment can be assigned to its respective origin, such as, for example, by substantial overlap in amino acid sequence, such as at least 5, at least 10, at least 20 consecutive amino acids.

The fragments according to the present invention are preferably obtained from bacilli grown under the stressful conditions of starvation, low oxygen and low pH. Low oxygen is due to the growth of the bacteria on plates which are closed in hermetic bags during the growth period, which is for example 21 days, which leads to a microaerobiotic environment. The low pH is explained as follows: At the beginning of culture the pH value is 7.0-6.8, and the end, after typically 21 day of culture, the pH value is 6.4-6.5). Under these conditions, the metabolism of the bacteria is slower, which leads to stationary growth. It is understood that this renders the bacilli more resistant to stress. Under such conditions cultured bacilli develop similar characteristics as in vivo latent bacilli in LTBI (Latent tuberculosis infection). The antigens present in FCMtb are thus expected to trigger a new immunological response against antigens of the latent bacilli, i.e. the so-called “structural” antigens as well as those associated to stress responses.

Mycobacterial glycolipids have long been recognized to have immunomodulatory activity, notably the induction of granulomatous responses and to exert potent adjuvant-like effects. Therefore, in a more preferred embodiment, the liposome formulation described above contains lipids which are typically found in *Mycobacterium tuberculosis*, or derivatives thereof, such as conjugation products like sugar conjugated lipids. Several immunogenic lipid components have been identified in *M. tuberculosis* samples (Brennan, Tuberculosis (Edinburgh), 2003, 83(1-3), 91-97) and analytical methods for their determination have been developed (electrophoresis, SDS-PAGE, thin layer chromatography). Although the isolation of each lipid component would require such an aggressive treatment that quantitative data or percentages of each component detectable in the MTB-C extract or in the liposome formulation are difficult to obtain, the qualitative characterisation shall serve to characterize a further preferred embodiment of this invention. According to this further preferred embodiment, one or more of mycolic acids, preferably belonging to any one or more of types I, III or IV is comprised. Alternatively or in addition, a sugar-conjugated mycolate, preferably trehalose dimycolate may be comprised in the formulation. Alternatively or in addition, a glycolipid lipoarabinomannan (LAM) may be comprised in the formulation. Furthermore the multiantigenic nature of the fragments (multiantigenic protein mixture plus lipids, instead of purified antigens alone) is believed to be an advantage and therefore the cell fragmentation process can be adapted by the skilled person so as to allow the optimal cellular antigen mixture.

Homogenisation of the MTB-C cells is carried out in the presence of one or more surfactants, preferably a nonionic surfactant. Hence, the liposome formulation described above may additionally comprise one or more such surfactants. A large number of such surfactants are within the standard knowledge of a person skilled in the art. Preferably, the nonionic surfactant used is selected from the group consisting of alkylphenol ethoxylates, and sorbitan ester ethoxylates. More preferably, the nonionic surfactant is selected from the group of octylphenol ethoxylates. Even more preferably, octylphenol ethoxylates with an ethylene oxide content comprised between 7 and 8 moles are used, which surfactants can be found on the market under the name Triton X-114®. The homogenised mass containing the cell wall fragments is subjected to a conventional treatment to separate and reject the non-fragmented cells and the solubilized components. Centrifugation at different speeds and washing with buffer solution as described in patent application ES2231037-A1 can be used for example. Sediment containing the cell wall fragments is obtained after performing the mentioned purification processes. Said sediment is dispersed in phosphate-buffered saline (PBS) buffer and is subjected to a conventional treatment to ensure the complete inactivation of the MTB-C cells which may have remained viable after the fragmentation and purification process. The mentioned treatment can be a chemical process, for example by means of treatment with formaldehyde, or a physical process, for example by means of autoclaving or pasteurisation treatment. Examples of lipid characterization are given in Example 5 below.

In a further preferred embodiment, the above described liposome formulation additionally comprises one ore more salts or solution(s) thereof, whereby the preferred salt is sodium chloride.

In an even more preferred embodiment of any of the above, the liposome formulation is freeze-dried. The liposomes can be subjected to lyophilisation to thus obtain the immunotherapeutic agent in the form of lyophilised liposomes. To that end, the dispersion can be distributed into vials and lyophilised at a low temperature, such as between −15° C. and −120° C., such as for example −45° C. and with a vacuum, such as between 0.1 and 0.5 mbar. The vials obtained after lyophilisation contain the liposome formulation suitable as immunotherapeutic agent and they are preferably stored at very low temperatures, for example at −70° C.

The invention also provides a suspension, wherein the liposome formulation of any of the preceding claims is reconstituted in a solvent. In a preferred embodiment, the solvent of this suspension is aqueous, more preferably and most preferably is or comprises physiological serum. Methods of suspending liposome formulations in a solvent are well known to the person skilled in the art. It is a particularly advantageous property of the formulation according to this invention that it can be suspended faster than conventional liposome formulations comprising MTB-C fragments (see Example 9)

One object of the invention is the provision of an agent comprising cell wall fragments of a strain of MTB-C for the preparation of a pharmaceutical composition, whereby the agent is or comprises the liposome formulation described above in any of the embodiments described or combinations thereof. The main scope of the pharmaceutical formulation/galenic formulation of the drug substance is to obtain a suspension effective and stable enough to be well recognized by the cells and which has the potential to trigger a relevant cellular immune response in a human or animal body. To that end, the invention also provides a pharmaceutical composition comprising the liposome formulation, or the suspension as described in any one or more of the embodiments described above, and a pharmaceutically acceptable carrier, excipient or diluent. Various such carriers, excipients and diluents are known to the person skilled in the art, and they are in no way limited by this disclosure. Rather, any substance suitable as carrier, excipient or diluent may be used. In a preferred embodiment, this pharmaceutical composition additionally comprises a pharmaceutically acceptable adjuvant. Adjuvant is thereby to be understood as a substance comprised in this embodiment of the invention, whereby the adjuvant is a substance capable of stimulating the immune system when applied to a human or animal body in response to the target antigen, whereby the adjuvant does not itself confer immunity. Without wishing to be limited to any particular adjuvant substance, preferred embodiments are wherein the adjuvant is an aluminium salt, such as aluminium chloride, or a mineral oil or a composition comprising mineral oil, such as incomplete Freund's adjuvant (IFA) or complete Freund's adjuvant (CFA), or an ammonium halogenide, such as an alkylated ammonium bromide, such as dimethyldioctadecyl-ammonium bromide.

The invention also provides a product for use in a method of treatment of the human or animal body by therapy. That is, it provides the liposome formulation according to any one or more of the embodiments described above, the suspension according to any one or more of the embodiments described above, or the pharmaceutical composition according to any one or more of the embodiments described above for use in a method of treatment of the human or animal body by therapy.

The drug can be administered in a mucosa, for example, ocular, intranasal, oral, gastric, intestinal, vaginal, or urinary tract mucosa, or parenterally, for example, subcutaneously, intradermally, intramuscularly, intravenously, or intraperitoneally. Parenteral administration is preferred. In a particular embodiment, the invention provides this liposome formulation, suspension or pharmaceutical composition for injection.

In another particular embodiment, the invention provides this liposome formulation, suspension or pharmaceutical composition for use in a method of treating or preventing tuberculosis. These particular embodiments may be met individually or in combination. The inventors of the present study have found that the formulation according to the present invention leads to increased cellular immune response and also controls the process of constant re-infection that may otherwise occur in latent tuberculosis infection, by boosting the immunity against growing bacilli and by inducing immunity against the non-replicating bacilli.

The suitable dose of the liposome formulation, suspension or pharmaceutical composition according to what is described above in relation to the use thereof in a method of treatment of the human body by therapy depends on several parameters, including the method of administration and the subject to be treated. In a preferred embodiment, it is for administration to the human body. In a preferred embodiment thereof, this occurs in a dose comprising 1 to 1000, preferably 3 to 250, more preferably 4 to 80, and most preferably about 5, about 25 or about 50 µg/dose FCMtb. A dose of 25 µg is particularly preferred.

In three more particular embodiments (a) to (c), the liposome formulation, suspension or pharmaceutical composition according to what is described above in relation to the use thereof in a method of treatment of the human or animal body by therapy is (a) for use in a method of prevention of active tuberculosis in individuals with a latent tuberculosis infection. In an alternative more particular embodiment, (b) for use in a method of primary prophylaxis of tuberculosis in order to prevent infection of individuals who had been exposed to the disease, but are not yet infected or (c) for use in a method of treating or preventing latent tuberculosis.

The liposome formulation, suspension or pharmaceutical composition for the use thereof in a method of treatment of the human or animal body by therapy can be administered in the form of a single dose or of several, such as two, three, four, five or more than five, doses, by means of the repetition at certain time intervals. Preferably two doses are administered separated by a period comprised between 2 and 5 weeks, preferably between 3 and 4 weeks.

Examples 8, 10 and 12 are examples of how the liposome formulation according to this invention may be applied to human or animal subjects.

A preferred embodiment of the substance above is the liposome formulation, suspension or pharmaceutical composition for use in combination or adjunctive therapy. Medical practitioners use adjunctive therapy frequently to get better cure rates or a faster response to primary treatment. A combination therapy or adjunctive therapy involves using more than one medicine to treat the human or animal body by therapy. A first particular embodiment of a combination therapy is one wherein the combination therapy comprises an antibiotic, preferably one or more of isoniazide and an ansamycine, whereby the ansamycine is most preferably rifampicin. A second particular embodiment thereof is where the combination therapy comprises other prophylactic vaccines against tuberculosis, such as those mentioned in S. H. E. Kaufmann, Nature Rev. Immunol., 2006, 6, pages 699-704, such as for example the Bacillus Calmette-Guerin (BCG) vaccine, subunit vaccines or recombinant BCG vaccines. The first and second particular embodiment may be combined.

In combination therapy or adjunctive therapy, administration of these two (or more) substances can be simultaneous, or it can be done in two (ore more) inoculations separated over time. The period between the inoculations can even be several years long. In the case of a combination therapy, inoculations separated over time, first a prophylactic vaccine against tuberculosis is preferably administered, and the drug comprising the cell wall fragments of a virulent strain of MTB-C, which acts as a re-stimulating (boost) agent of the initially inoculated vaccine, is subsequently administered. In one embodiment, only a single dose is administered to the human subject, and this dose is preferably 25 μg FCMtb.

Alternatively, several different treatment strategies or types or care are employed simultaneously in adjunctive therapy. In a particular embodiment of the present invention, adjunct therapy is administered to a human subject with an impaired immune system, such as an individual suffering from HIV, or any individual otherwise prone to tuberculosis infection and/or in need of such therapy. Isoniazid may also be administered in the adjunctive therapy. Further, the adjunctive therapy may comprise administration of any drug or combination of drugs to treat the impaired immune system, such as to treat the HIV infection. Typical drugs to treat HIV infections are antiretroviral drugs, and a non-liming overview can be found in: "Antiretroviral therapy for HIV infection in adults and adolescents Recommendations for a public health approach: 2010 revision", Authors: World Health Organization, ISBN: 9789241599764.

Thus, the present inventors have provided a solution for the need of providing effective tuberculosis protection, such as vaccination, to HIV positive human subjects.

Whether an individual is to be considered HIV positive or not (i.e. HIV negative) can be tested by any test which allows detection of the presence of the human immunodeficiency virus (HIV), the virus that causes acquired immunodeficiency syndrome (AIDS), in a body fluid from the individual to be tested, wherein the body fluid is typically any one selected from serum, saliva, or urine. Such tests may detect antibodies, antigens, or RNA. An overview of suitable screening test is given in Chou et al., Ann. Intern. Med. 2005 Jul. 5; 143(1):55-73.

The inventors of the present invention have surprisingly found that a single dose of 25 μg FCMtb administered to a HIV positive human subject provides a strong response.

A single dose of 25 μg FCMtb was also powerful when administered to a HIV negative human subject. The present inventors showed that this is particularly useful in subjects suffering from latent tuberculosis (Example 12). Thus, a single dose of 25 μg FCMtb to be administered to a HIV positive or a HIV negative individual is a preferred embodiment of the invention.

The invention also provides a method of manufacture, characterized in that it is suitable for obtaining a liposome formulation according to any one or more of the embodiments described above, as well as of a suspension, or pharmaceutical composition comprising the same. One non-limiting Example thereof is given as Example 11 below.

The invention further provides the MTB-C strain NCTC 13536, deposited in 2010 at the NCTC in London. The strain has a low genetic polymorphism. Therefore, formulations comprising fragments of NCTC 13536 have the advantage of very high reproducibility because of the low genetic polymorphism.

PREFERRED MODE OF CARRYING OUT THE INVENTION

It is preferred that specific doses of 50 μg FCMtb/dose, or 25 μg FCMtb/dose or 5 μg FCMtb/dose are used. For example, when the dose is 50 μg FCMtb, the amounts/substances given in Table 1 are present in one vial of the formulation:

TABLE 1

| COMPONENTS | UNIT PER VIAL | FUNCTION |
| --- | --- | --- |
| DRUG SUBSTANCE | | |
| FCMtb | 66.7 μg | Immunogen |
| Further components | | |
| Sucrose | 20,000.0 μg | Charge substance (freeze-drying) and cryoprotector |
| Soy lecithin [1] | 845.8 μg | Liposome forming agent |
| Sodium cholate | 92.0 μg | Tensoactive |
| Sodium chloride [2] | 20.8 μg | Solvent |
| Particle characterization | | |
| z-average particle size | 75 +/− 20 nm | |
| Polydispersity index | ≤0.350 | |

[1] Containing Phosphatidylcholine (94.0% (w/w))
[2] Added as NaCl 0.9% solution.

For 25 μg/dose or 5 μg/dose application, other vials are prepared, wherein all number values shown in Table 1—except sucrose—are to be divided by the factor of 2 or 10, respectively. The content of sucrose in the formulations (50 μg, 25 μg and 5 μg) is always 20.000 μg unit/vial.

A liposome formulation made of soy lecithin (liposome forming agent) highly enriched with phosphatidylcholine (94.0% (w/w)) and sodium cholate (tensoactive agent) has shown to be adequate to guarantee greater solubility of the drug substance during manufacture as well as in the reconstituted suspension. One important parameter for stability of the FCMtb in the liposome formulation is the proportion of the components which constitute the liposome. After testing different ratios of FCMtb/lipid component, it was established that a very good ratio is approximately 0.03:0.2:0.7 (FCMtb:sodium cholate:soy lecithin, w/w/w). It was further observed that the liposome formation was enhanced by the presence of salts in the aqueous phase. Therefore, sodium chloride is included in this particular formulation.

TABLE 2

Drug product (FCMtb), measured after reconstitution of the lyophilized liposome composition

| | Parameter | | Acceptance criteria | Test methods |
| --- | --- | --- | --- | --- |
| Appearance | | | White to off-white powder | Visual inspection |
| Cake morphology | | | Flat to almost flat and homogeneous | Visual inspection |
| Dosage uniformity | Mass uniformity (mg/vial) | | 21.02 ± 15% | Weighing, in house method |
| | Mass mean (mg/vial) | | Mass ± 5% | Weighing, in house method |
| Water content (%) | | | ≤3% | Karl Fischer coulometric assay, European Pharmacopeia method 2.5.12 (United States Pharmacopeia method <921>) |
| Total protein content of FCMtb | | | 90-140 μg/mg FCMtb | BCA assay, European Pharmacopeia method 2.5.33 (United States Pharmacopeia method <1057>) |
| Time to reconstitution (s) | | | Well reconstituted ≤10 s | Visual inspection |
| pH | | | 7-8 | Potentiometry, European Pharmacopeia method 2.2.3 (United States Pharmacopeia method <791>) |
| Particle size | z-average (nm) | | 75 ± 20 | Dynamic light scattering European Pharmacopeia method 2.9.31 |
| | (Polydispersity index) | | (≤0.310) | |
| Immunogenic potency in *M. Tuberculosis* infected murine model | Antigen-specific IFN-γ Spot forming units | PPD | 3-12 Ratio SFU/$10^6$ cells with respect to basal value (Basal value in SFU/$10^6$ cells) | ELISpot |
| Protein profile | SDS-PAGE | | Positive for bands: 70, 38, 30, 10, 6 kDa | Electrophoresis by SDS-PAGE |
| | Western-blot | | Positive for HSP70 (Rv0350), 38 kDa (Rv0934), Ag85B (Rv1886c) | Western-blot |
| Sterility | | | Sterile | European Pharmacopeia method 2.6.1 (United States Pharmacopeia method <71>) |
| Bacterial endotoxins (IU/dose) | | | ≤10 IU/vial | European Pharmacopeia method 2.6.14 method D (United States Pharmacopeia method <85>) |

In a preferred mode the invention is carried out such that the liposome formulation according to this invention has the properties according to Table 2.

For administration to living subjects, the vial can be reconstituted with 0.4 ml of water for injections to give a suspension containing 166.7 µg/ml of FCMtb.

Table 3 shows the concentration of each component per vial after reconstitution at 50 µg/dose. For 25 µg/dose or 5 µg/dose application, other vials are used, so that in line with what is said above about Table 1, all number values shown in Table 3—except sucrose—are to be divided by the factor of 2 or 10, respectively. The content of sucrose in the formulations (50 µg, 25 µg and 5 µg) is always 50.000 ug/mL

TABLE 3

Concentration of components after reconstitution in 0.4 mL water for injection

| Components | Concentration per mL |
|---|---|
| DRUG SUBSTANCE | |
| FCMtb | 166.7 µg/mL |
| EXCIPIENTS | |
| Sucrose | 50,000.0 µg/mL |
| Soy lecithin | 2,114.4 µg/mL |
| Sodium cholate | 230.0 µg/mL |
| Sodium chloride | 52.1 µg/mL |

Materials and Methods
Reference Materials
a) Monoclonal antibodies: Specific monoclonal antibodies (anti-HSP70, anti-38 kDa, anti-Ag85B, (from Lionex Diagnostic GmbH, Braunschweig, Germany)) are used for the identification of the protein profile of FCMtb batches.
b) Albumin Standard: This standard, used for the determination of protein content, is composed of bovine albumin in 0.9% of saline solution (2 mg/ml), conserved in sodium azide (manufacturer: Pierce).
c) Trehalose 6,6'-dimicolate from *Mycobacterium tuberculosis* (TDM) standard: Commercially available TDM (Sigma) is used for the identification of TDM of FCMtb batches.
d) Mycolic acids from *Mycobacterium tuberculosis* standard
   A commercially available mycolic acid (Sigma) is used for the identification of mycolic acid of FCMtb batches.
e) Molecular weight marker: A commercially available molecular weight marker named SeeBlue® Plus prestained Standard" (Invitrogen) is used.
Determination of Parameters
a) pH
   The pH of the reconstituted suspension of FCMtb (20 mg/ml) is determined by potentiometry according to European Pharmacopeia method 2.2.3 and United States Pharmacopeia method<791>.
b) Water content
   The test for the determination of residual water of the lyophilized FCMtb is carried out using Coulometric Karl Fisher equipment, and it follows the general indications of the European Pharmacopeia, method 2.5.12, and United States Pharmacopeia method <921> Water determination.

c) Determination of total protein content
   The test for the determination of total protein content of the FCMtb is carried out using a commercial kit (BCA kit, Pierce) and following European Pharmacopeia, method 2.5.33, method 4 (Bicinchoninic acid or BCA assay) and United States Pharmacopeia method <1057>.
d) Identification of protein profile by sodium dodecyl sulphate polyacrylamide gel electrophoresis (SDS-PAGE)
   The test is performed according to European Pharmacopeia, method 2.2.31 and United States Pharmacopeia method <726>; the detection of proteins in the gel is performed by an adapted Coomassie staining or by Silver staining. Test samples: Reconstitute FCMtb in purified water at 40 or 20 mg/ml concentration. Reference solutions: Molecular weight marker, Purified antigens, FCMtb reference standard

TABLE 4

| Reference antigens Purified Antigens |
|---|
| *M. tuberculosis* HSP70 protein (Rv 0350) |
| *M. tuberculosis* 38 KDa protein (Rv0934) |
| *M. tuberculosis* Ag85B protein (Rv1886c) |
| *M. tuberculosis* 19 kDa protein (Rv 3763) |
| *M. tuberculosis* CFP10 protein (Rv3874) |
| *M. tuberculosis* ESAT6 protein (Rv3875) |

For Coomassie staining, Gel-Code Blue Stain reagent solution (Pierce) is used according to the manufacturer's instructions. For Silver Staining, the PROTSIL1 Kit from Invitrogen is used according to the manufacturer's instructions. For Western Blot analysis, proteins are separated by SDS PAGE according to standard methods known in the art and then electrophoretically transferred onto a PVDF membrane for immunodetection using specific monoclonal antibodies. The interaction antigen-antibody is visualized by incubation with an anti-antibody which triggers a chemiluminescent reaction. Antigens from Lionex (Braunschweig, Germany) (*M. tuberculosis* HSP70 protein (70 kDa), *M. tuberculosis* 38 kDa protein, *M. tuberculosis* Ag85B protein (30 kDa), and specific monoclonal antibodies anti-HSP70, anti-38 kDa, and anti-Ag85B from Lionex are used.
e) Identification of mycolic acids
   Mycolic acids in FCMtb are examined by one-dimensional TLC, following the European Pharmacopeia, method 2.2.27. Test samples: Lyophilised FCMtb, 40 mg. Reference solutions: Mycolic acid standard (Sigma). Procedure:
   a) Extraction process: The sample is extracted with chloroform:methanol (1:1) and then it is incubated overnight. The supernatant fraction is eliminated.
   b) Mycolic acid esterification: 2 mL of methanol: toluene:sulphuric acid (30:15:1; vol/vol) is added on each tube, and esterification is achieved overnight. Then, 4 mL of n-hexane is added. It is dried under nitrogen flow and it is resuspended with 500 µl hexane.
   c) TLC: 10 µl of each sample is applied on a line parallel to the edge of the plate (Silica gel 60 (20×20 cm) (Merck). The chromatographic separation is performed in a saturated tank with a mobile phase (ethylic ether:n-hexane (15:85, vol/vol)) by three times. Then, the plate is allowed to dry in air.

d) Mycolic acids are revealed by spraying the plates with a solution of phosphomolybdic acid in 96° ethanol and heat at 120° C. for 10 min.

Mycolic acids in FCMtb samples are determined by comparison with mycolic acid commercial standard spot. Results are expressed as qualitative data (presence (positive)/absence (negative) of mycolic acid assessed.

f) Identification of trehalose 6,6'-dimycolate (TDM): Test samples: Lyophilised FCMtb, 40 mg. Reference solutions: TDM standard (Sigma). Procedures (i) Extraction process: The sample is extracted with chloroform:methanol (1:1; vol/vol) and then it is incubated overnight. The supernatant fraction is dried under nitrogen flow and it is weighted. Finally, dried samples are resuspended in chloroform at 40 mg/mL final concentration.

(ii) TLC: 10 μl of each sample is applied on a line parallel to the edge of the plate (Silica gel 60 (20×20 cm) (Merck). The chromatographic separation is performed in a saturated tank with a mobile phase (chloroform: methanol:water (60:12:1; vol/vol). Then, the plate is allowed to dry in air.

(iii) Detection: The TDM is revealed by spraying the plates with a solution of antrone 1% in sulphuric acid and heat at 120° C. for 5 minutes.

(iv) Identification: TDM in FCMtb samples is determined by comparison with commercial TDM which is used to generate a standard spot. Results are expressed as qualitative data, i.e. presence (positive)/absence (negative) of TDM assessed.

g) Identification of lipoarabinomannan (LAM): For Western Blot analysis of LAM, compounds are separated by SDS PAGE according to standard methods and then electrophoretically transferred onto a nitrocellulose membrane for immunodetection using specific antibody CS35. The interaction antigen-antibody is visualized by incubation with an anti-antibody (IgG Goat anti-mouse IR Dye 800 CW) which triggers a fluorescent reaction.

h) Sterility

All processes which require sterility, according to the knowledge of the person skilled in the art, are carried out under sterile conditions; this also applies if sterility is not explicitly mentioned for any given step which requires the same. Sterility test is assessed as prescribed in European Pharmacopeia method 2.6.1 (USP <71>).

i) Mycobacteria inactivation

The inactivation of mycobacteria is assessed in accordance with European Pharmacopeia method 2.6.2 j) Bacterial endotoxins

The test for bacterial endotoxins (LAL test, Limulus Amoebocyte Lysate) is performed according to the general indications of the European Pharmacopeia, method 2.6.14, following Method D (Chromogenic kinetic method) as well as United States Pharmacopeia method <85>.

Fragmentation of the Bacilli

The choice of fragmentation of the bacilli is thought to allow optimal presentation of cell antigens, particularly cell wall antigens. Fragmentation of the FCMtb is determined by both Dynamic Light Scattering (as described below) and Laser diffraction methodologies.

Laser diffraction allows measuring the fragmentation in a range between 0.04 μm and 2000 μm. The assay is carried out in the Servicios Científico-Técnicos de la Universitat de Barcelona, Spain. Instrument: Coulter LS 13320 equipped with a Universal Liquide Module (ULM). Solvent: purified water/mineral oil. Results: plotted as a histogram, expressing the relative frequency of the number of particles (%) in front of the particle diameter (0.04 μm-2000 μm).

Determination of z-Average Particle Size and Polydispersity Index

The average particle size as described in this document is determined by dynamic light scattering (DLS), which is based on the physical concept of the Brownian motion of particles, defined in the Stokes-Einstein equation:

$$d(H) = \frac{kT}{3\pi\eta D}$$

where:—

(H)=hydrodynamic diameter

D=transiational diffusion coefficient k=Boltzmann's constant

T=absolute temperature

η=viscosity

Without wishing to be limited to any particular theory, the Stokes-Einstein equation establishes that particles suspended in a liquid medium are in a constant and random movement, with a speed that depends on their size: the larger the particle is, the slower the Brownian motion will be.

In dynamic light scattering measurements, the sample containing the particles to be measured is illuminated with a monochromatic light source, preferably a laser, and analyzed in a correlation function how the intensity of scattered light fluctuates with time. If, for instance, large particles are being measured, as they move slowly, the intensity of scattered light fluctuates slowly, and the correlation takes long time to decay; on the other hand, if small particles are being measured, as they move quickly, the intensity of scattered light fluctuates quickly, and the correlation of signal decays more rapidly.

According to this invention, the particles are preferably measured with the following instrument: Zetasizer nano zs (Malvern Instruments), using purified water/mineral oil as solvents.

If nothing to the contrary is indicated, the instrument is used according to the manufacturer's instructions, and adjustment and calibration, if applicable, are also according to the manufacturer's instructions.

The size is calculated from the correlation function using various algorithms. In the present case, the 'cumulants analysis', as defined by the International Organization for Standardization (ISO) for "Particle size analysis—Photon correlation spectroscopy", is applied. The correlation function fits results in a single exponential curve that allows for calculation of the following parameters:

The mean size, or z-average diameter, of the particle distribution. This mean size is the intensity mean.

The polydispersity index (pdi), i.e. corresponding to the width of the particle size distribution.

The results are typically plotted as a histogram, expressing the relative frequency of the number of particles (%) with respect to the particle diameter which may be any diameter which is comprised in the range from 1 nm to 3 μm.

Potency Tests

Specific-pathogen-free, 6-7-week-old female C57BL/6 mice are provided by Harlan Iberica (Spain). Test sample: formulation of table 3 and placebo (vaccine formulation without active component).

a) In vivo *M. tuberculosis* infected murine model vaccinated with a single dose: The experimental design consists of:

Day 0: Subcutaneous infection on lower abdomen of mice with Mtb strain H37Rv Pasteur (4×104 CFUs). Day 14: Chemoprophylactic treatment of the animals with a single oral dose of rifapentine (25 mg/kg) and Isoniazid (10 mg/kg) thus leading to an antibiotic effect of 1 week. Day 21: Vaccination with a single dose of vaccine/Placebo and/or H2O subcutaneously in the neck. All the samples are obtained and analyzed for individual mice. Each experiment includes: a basal group of infected mice plus placebo and the experimental group of infected mice plus vaccination. The groups consist of 6-7 animals, and the experiments are performed in duplicate. Day 28: Animals are anesthetized with isofluorane.

b) In vivo *M. tuberculosis* infected murine model vaccinated with two doses: The experimental design consists of: Day 0: Subcutaneous infection on lower abdomen of mice with Mtb strain H37Rv Pasteur (4×104 CFUs). Day 14 Chemoprophylactic treatment of the animals with a single oral dose of rifapentine (25 mg/kg) and Isoniazid (10 mg/kg) thus leading to an antibiotic effect of 1 week. Day 21 Vaccination with a first dose of vaccine/Placebo and/or H2O subcutaneously in the neck. Day 36: Vaccination with a second dose of vaccine/Placebo and/or H2O subcutaneously in the neck. All the samples are obtained and analyzed for individual mice. Each experiment includes: a basal group of infected mice plus placebo and the experimental group of infected mice plus vaccination. The groups consist of 6-7 animals, and the experiments are performed in duplicates. Day 42 Animals are anesthetized with isofluorane.

For both a) and b) above, following sacrifice, the ex vivo analysis of interferon-γ Spot Forming Units (SFU) parameter by ELISPOT is performed using spleen cell suspensions for cellular immune response.

Determination of immunogenic potency in *M. tuberculosis* healthy murine model. Specific-pathogen-free, 6-7-week-old female C57BL/6 mice are provided by Harlan Iberica (Spain). In vivo *M. tuberculosis* healthy murine model vaccinated with two doses. The experimental design consists of: Day 0 Vaccination with a first dose vaccine according to the preferred mode of carrying out this invention, or Placebo and/or $H_2O$ subcutaneously in the neck. Day 21 Vaccination with a second dose of vaccine/Placebo and/or H2O subcutaneously in the neck. All the samples are obtained and analyzed for individual mice. Each experiment includes: a basal group of healthy mice plus placebo and the experimental group of healthy mice plus vaccination. Day 28 Animals are anesthetized with isofluorane. After sacrifice, the analysis of IgGs antibodies by ELISA is performed using mouse serum for humoral immune response.

Diagnosis of Tuberculosis

Methods for diagnosis of tuberculosis are well known to the skilled person. The Quantiferon test and the TST are known to deliver reliable results and may be used alone or in combination for categorizing subjects for their suitability to be subjected to therapy with the product of the present invention. QuantiFERON, also known as QFT, is a commercially available test for tuberculosis infection or latent tuberculosis, manufactured by Cellestis Limited, Chadstone, Melbourne, Victoria, Australia. QFT is an interferon-γ release assay (IGRA) used in tuberculosis diagnosis. It is used according to the manufacturer's instructions. The Mantoux test (also known as the Mantoux screening test, Tuberculin Sensitivity Test, (TST test), Pirquet test, or PPD test for Purified Protein Derivative) is a diagnostic tool for tuberculosis. An overview of both tests can be found in Franken et al., Clin Vaccine Immunol. 2007, April; 14(4): 477-480.

EXAMPLES

The Examples below are given to provide the person skilled in the art with a workable mode and explanation of some specific embodiments of the invention. These Examples have illustrative purpose and do by no means intend to limit the scope of the invention in any way.

Example 1: Isolation of the Strain *Mycobacterium tuberculosis* NCTC 13536

The starting material for the production of FCMtb is an inoculum of the strain NCTC 13536, synonymously called 511 or *Mycobacterium tuberculosis* NCTC 13536, a strain of *Mycobacterium tuberculosis* isolated from an immunocompetent patient diagnosed with pulmonary tuberculosis in Barcelona, Spain. It was deposited in 2010 at the NCTC in London, which is an official depositary organisation according to the Budapest Treaty. The strain has additionally been deposited by the strain collection of the Service of Microbiology of the Hospital de Sant Pau, Barcelona, Spain.

Two passages of the original strain have been performed in the years 1995, and 1996 respectively. MSL PB#1 corresponds to the second passage of the original strain of *M. tuberculosis* NCTC 13536, which was performed in October 1996 resulting in 100 vials (3 ml sterile glass vials) stored at −70±5° C. The strain has a low genetic polymorphism, as identified by standard methods in the art.

Example 2: Upstream Process for Production of MTB-C Cells

A flow-chart of this process is given in FIG. 1. The starting material for the production of FCMtb is an inoculum of the strain *Mycobacterium tuberculosis* NCTC 13536 (Example 1). In order to ensure the continued supply of this starting material, a seed lot system is preferably used. Hence, a working seed lot (WSL) derived from a master seed lot (MSL) is used for production of FCMtb. *Mycobacterium tuberculosis* NCTC 13536 (Example 1) is cultured for 3-5 weeks in Löwenstein-Jensen medium. The bacterial growth is then sub-cultured in Proskauer Beck media at 37±2° C. with stirring at 100±5 rpm. Once the maximum bacterial concentration (by visual inspection) is achieved, a subculture in Proskauer Beck media is started and incubated. When a similar bacterial concentration is achieved, small aliquots are taken. The viable bacterial count is determined by the number of colony forming units (CFUs) obtained in Middlebrook agar medium after incubation at 37±2° C. for 3-4 weeks. The bacterial count must be $2-5\times10^7$ CFUs/ml.

(1) Culture of *Mycobacterium tuberculosis*

The production of FCMtb begins with the seeding of 0.2 ml of a WSL in a 7H11 agar plate and incubation at 37±1° C. for 15±2 days. Then, colonies are transferred into a tube containing a few glass beads. After mixing, approximately 5 ml of water for injection (WFI) is added to obtain a bacterial suspension. At this point, a viable plate count and a sterility test are performed. About 100 Middlebrook 7H11 agar plates are seeded with *M. tuberculosis* using swabs soaked with the bacterial suspension to obtain confluent cultures. The plates are incubated at 37±1° C. for 21±2 days.

Sterility Test as in-Process Control is Performed as Follows:

The sterility testing is aimed to ensure the absence of fungi and bacteria other than Mycobacteria. The tests are carried out by direct inoculation, following the conditions described in Ph. Eur 2.6.1 for the sterility test. Samples tested must be sterile. Medium 7H11 is used instead of 7H10 (as is mentioned in European Pharmacopeia method 2.6.2). 7H11 is based on medium 7H10 adding one gram of pancreatic digest of casein in order to enhance the growth of strains of Mycobacterium tuberculosis.

(2) Harvest of *Mycobacterium tuberculosis* and Freezing of Crude Extract

After the incubation period, the purity of the bacterial culture is controlled by a visual inspection of the agar plates and the performance of a sterility test. Then, bacterial growth is collected from agar plates and transferred into a sterile tube. The crude extract obtained is weighed (20-22 g). The mixture is kept at −80° C.±5° C.

Example 3: Downstream Process for Production of Liposomes Obtained from the Crude Extract A flow-chart of this process is given in FIG. 2.

(3) Cell Fragmentation and De-Lipidation

The frozen crude extract (Example 2) is thawed at 37±1° C. and sterile PBS buffer with 4% (w/w) Triton-X114 (pH 7.0-7.5) is then added at 4° C. After mixing, it is subsequently transferred into a sterile polycarbonate container containing sterile silica/zirconia beads. Then, cell fragmentation is carried out in a Beadbeater by applying the following fragmentation method: 3 cycles, each one consisting of 5 periods ON/OFF plus 10 minutes of break. Once the process is finished, the cellular fragmented fraction is separated from the beads by subsequent washings (repeated shaking and sedimentation) in sterile PBS buffer with 4% triton-X114, (pH 7-7.5). An aliquot of the washed suspension of the cellular fragmented fraction is then collected for pH control and a final centrifugation at 845 g at 4° C. for 30 minutes proceeds.

To remove the cytosolic fraction and to obtain a suspension enriched in cellular fragments, a high speed centrifugation is performed twice at 20000 g approx. for 60 minutes, at 4° C. After the first centrifugation, the yellowish supernatant (rich in soluble proteins and lipids) is discarded and the pellet is resuspended in PBS and further centrifuged under the same above described conditions. After that, the appearance of the discarded supernatant must be clear and colourless. Finally, the obtained pellet is resuspended in a final volume of 50-60 ml PBS (FCMtb suspension)

(4) Pasteurization

The FCMtb suspension is then pasteurized at 65±2° C. for 60 min. Once pasteurization is finished pH of the pasteurized FCMtb is determined by litmus paper. It is considered acceptable in the range pH 6.5-7.5. Sterile and depyrogenated vials are filled with 0.5 ml of the product suspension and IPCs on Sterility and Mycobacteria inactivation are performed. Finally, filled vials are frozen at −80±5° C. Once the material is subjected to pasteurisation, it will be physically segregated from untreated material, i.e. the spaces used before pasteurisations are clearly separated from those used during the subsequent filling process.

(5) Freeze-Drying

All vials containing the product frozen are then lyophilised at about −45° C. to 30° C. temperature and at 0.310 mbar pressure for approximately 18 hours (0.5 ml volume per vial). Using aseptic techniques and under $N_2$ atmosphere, the vials are stoppered and labelled. The packaged drug substance is then stored at −20°±5° C. for up to 12 months.

Example 4: Protein Characterization

FIG. 3 gives an overview of the characterisation strategy in terms of protein profile.

Based on literature (Andersen P., 1997, Scand J. Immunol.; 45(2):115-31; Geisel et al., 2005, J. Immunol.; 174(8): 5007-15; Stewart et al. 2005, Infect. Immun., 73(10):6831-7., Wang et al., 2007, J. Mol. Biol., 366(2):375-81), 6 protein bands were selected as being representative for protein profile assessment: HSP70 protein (Rv0350), 38 kDa protein (Rv 0934), (Rv 1866c), 19 kDa protein (Rv 3763), CFP10 protein (Rv3874), and ESAT-6 protein (Rv3875).

A. Determination of total protein content: Total protein levels in FCMtb are quantified by bicinchoninic acid (BCA) methodology. Total protein represents about 10% (w/w) of FCMtb content. Reference standards FCMtb-0429-16 and FCMtb-52.1 contain 167 μg protein/mg FCMtb and 115 μg protein/mg FCMtb, respectively.

B. Identification of protein profile by sodium dodecyl sulphate polyacrylamide gel electrophoresis (SDS-PAGE): The protein profile of the drug substance FCMtb was determined by comparison with reference antigens from *Mycobacterium tuberculosis* corresponding to ESAT6 (6 kDa) (7); CFP10 (10 kDa) (6); Ag85B (30 kDa) (1); 38 kDa (2); HSP70 (70 kDa) (4) as well as Molecular Weight marker MW (5), are shown (see FIG. 4). Determination of protein profile of drug substance FCMtb and identification of bands (approximately 70 kDa, 38 kDa, 30 kDa, 10 kDa and 6 kDa) is carried out by Coomassie staining. Identification of the 19 kDa band (lipopolypeptide) is carried out by silver staining.

C. Identification of the protein profile by Western-blot with specific monoclonal antibodies: The protein profile of the drug substance FCMtb is determined by the patterns obtained using Western-blot analyses with monoclonal antibodies (mAb): Anti-HSP70 (70 kDa, FIG. 5c), anti-38 kDa (FIG. 5d), anti-Ag85B (30 kDa, FIG. 5e).

FCMtb-52.1 is the reference batch for FCMtb according to the preferred mode of carrying out this invention.

Example 6: Lipid Characterisation

The characterisation of the lipid profile of FCMtb consists of a fractionating process based on chloroform:methanol (1:1) extraction. The fractionating process carried out in these studies has been based on the procedure described by Delmas et al., 1997, Glycobiology 7(6), 811-7. Thin layer chromatography (TLC) has been the method used to analyse the content of lipids and glycolipids present in FCMtb. Specifically, polyaciltrehalose (PT), trehalose dimycolate (TDM), diacyltrehalose (DAT), phosphatidilinositolmannosids (PIMs) and other phospholipids, as well as phthiocerol dimycocerosates (PDIM) and Mycolic acids have been identified by thin layer chromatography (TLC) both in the reference strains H37rv and NCTC 13536, as well as in different FCMtb batches. See FIG. 7a. The content of trehalose 6,6'-dimycolate (TDM) is analysed by TLC in the supernatant. Mycolic acids determination is conducted in the sediment, following a TLC method. Although no quantitative data are known for the lipid profile of MTB-C, the qualitative lipid profile established in the studies is in line with current scientific knowledge and allows for a standard characterisation of the immunogenic lipids so far known. FCMtb have been compared with whole cell lipid fraction of strains NCTC 13536 and H37Rv of *M. tuberculosis* and TDM commercial standard (see FIGS. 7a and 7b). Overall, the lipid content has been shown to be consistent in different batches of FCMtb-comprising liposomes according to this invention. FIG. 7d shows the identification of LAM.

Example 6: Characterization of Fragmented Cell Material

Preliminary results using both methodologies show that the fragments size of FCMtb is mainly below 1 µm (99%<1 µm) which is corroborated by FCMtb electronic microscopy: the fragment size ranges mainly from 100 to 300 nm.

Levels of residual DNA after extraction with a phenol/chloroform mixture have been investigated by absorbance at 260 nm (detection limit: 0.2 µg DNA/mg FCMtb). Typical results obtained so far are below 15 µg DNA/mg FCMtb.

The consistency of the production process of the drug substance is shown by a lipid and protein profile that is reproducible for different FCMtb batches.

Example 7: Immunisation of Mice and Visualization of Biological Activity

Interaction of protein bands of FCMtb with mouse immunoserum: Using Western-blot methodology it has been possible to visualize FCMtb protein bands that interact with IgG antibodies present in serum obtained from infected mice inoculated twice with the liposome-formulation based vaccine according to this invention. This is considered to be an indicator for the biological activity (FIG. 6).

Example 8: In Vivo Activity of a Liposome Formulation Comprising FCMtb

The biological activity of the vaccine is studied in an in vivo model by evaluating the immunogenic potency of FCMtb without liposomes (reconstituted with water for injection, WFI) and with FCMtb in the liposome formulation according to the best mode of carrying out the present invention (5% sucrose, see above) (FIG. 8). These results show the advantages of the liposome formulation with sucrose.

The aggregation or fusion states of liposomes are parameters which have been demonstrated to have a significant impact on the biological activity of the vaccine. Therefore, the researchers of the present invention perform an exhaustive control of particle size and polydispersity index during the manufacturing and at batch release of the vaccines.

Example 9: Effect of Sucrose

In an initial test, one of the following excipients (a) 1.5% glycine and (b) 5% sucrose, respectively, was optionally incorporated into a liposome formulation comprising fragments of the MTB-C strain NCTC 13536. Subsequently, a comparative evaluation is undertaken on physicochemical properties and biological activity associated to both formulations.

Results obtained by measurement after reconstitution of the lyophilized liposome composition and after testing according to the current batch release specification parameters are presented in Table 5.

TABLE 5

Results of specifications for 3 different formulations, measured after reconstitution of the lyophilized liposome composition.

| Parameter | | Acceptance criteria | | FCMtb formulated in a liposome suspension: Without excipient | Sucrose 5% | Glycine 1.5% |
|---|---|---|---|---|---|---|
| | | | | FCMtb formulated in a liposomal suspension | | |
| Appearance | | White to off-white powder | | ND | Complies | Complies |
| Cake morphology | | Flat to almost flat and homogeneous | | ND | Complies | Complies |
| Water content (%) | | ≤3% | | ND | 1.4 | 3.0 |
| Time to reconstitution (s) | | Well reconstituted ≤10s | | ND | 5 | 12 |
| pH | | 7-8 | | 8.1 | 7.4 | 7.0 |
| Particle size | z-average (nm) Pdi[(a)] | 75 ± 20 (≤0.250) | | 370[(1)] (0.492) | 66 (0.215) | 504 [(1)] (0.569) |
| Immunogenic potency in *M. Tuberculosis* infected murine model | Antigen-specific IFN-γ Spot forming units | PPD | 3-12 Ratio SFU/$10^6$ cells with respect to basal value (Basal value in SFU/$10^6$ cells) | 3.6 (183) | 5.1 (183) | 2.8 (183) |
| | | Ag85B (30 kDa) | 5-20 Ratio SFU/$10^6$ cells with respect to basal value (Basal | 5.5 (73) | 9.6 (73) | 5.4 (73) |

TABLE 5-continued

Results of specifications for 3 different formulations, measured after reconstitution of the lyophilized liposome composition.

| | | FCMtb formulated in a liposome suspension | | |
|---|---|---|---|---|
| Parameter | Acceptance criteria | Without excipient | Sucrose 5% | Glycine 1.5% |
| | | FCMtb formulated in a liposomal suspension | | |
| | value in SFU/$10^6$ cells) | | | |

[a] Polydispersity index
[1] Presence of liposomal aggregates
ND = not determined The investigators of this study surprisingly found that 5% sucrose formulation provides the advantage of better physicochemical results, such as water content or time to reconstitution, respectively. But the most crucial fact is the important reduction in liposomal aggregation (particle size, z-average) shown with the sucrose-comprising formulation in comparison with the other two formulations. Analysis by Dynamic Light Scattering has shown a z-average of 75±20 nm (polydispersity index 0.350) of the sucrose-containing liposomes. Electron microscopy of freeze-fracturing preparations of the sucrose-containing liposome formulation shows a mixture of multilamellar and unilamellar liposomes with sizes between 40 and 100 nm (FIG. 9).

Due to this improved parameter together with the observed lesser water content levels (≤2%) for the 5% sucrose formulation, improved stability results are expected for this formulation. This is indeed the case. Data of the investigators of the present study of experimental batches formulated with 1.5% glycine stored at room temperature for 3 months have indicated a drastic loss of biological activity for PPD (immunogenic potency). By contrast, the biological activity for PPD remains basically unchanged when the 5% sucrose-comprising formulation is studied after 3 months storage at room temperature. Hence, sucrose also provides the advantage of better maintenance of the biological activity.

Example 10: Biological Properties of the Sucrose-Comprising Formulation

The formulation according to Table 3 was used for biological studies. The cellular immune response triggered by inoculation of vaccine according to the preferred mode of carrying out this invention (single inoculation) in a *Mycobacterium tuberculosis* infected murine model can be measured by ELISPOT, results are given in Table 6.

TABLE 6

Cellular response after inoculation in mice.

| | | Batch (50 μg/dose, 166.7 μg/mL) | | | |
|---|---|---|---|---|---|
| | Parameter | a09 | c09 | d09 | e09 |
| Antigen-specific IFN-γ Spot forming units (SFU) | PPD Ratio SFU/$10^6$ cells with respect to basal value (Basal value: SFU/$10^6$ cells) | 5.1 (Basal: 183 SFU/$10^6$ cells) | 6.3 (Basal: 98 SFU/$10^6$ cells) | 7.2 (Basal: 164 SFU/$10^6$ cells) | 6.5 (Basal: 164 SFU/$10^6$ cells) |
| | Ag85B Ratio SFU/$10^6$ cells with respect to basal value (Basal value: SFU/$10^6$ cells) | 9.6 (Basal: 73 SFU/$10^6$ cells) | 9.9 (Basal: 44 SFU/$10^6$ cells) | 11.9 (Basal: 90 SFU/$10^6$ cells) | 12.3 (Basal: 88 SFU/$10^6$ cells) |

ND: Not determined.

Inoculation of the liposome formulation based vaccine leads to a significant increase of cellular immune response in vivo compared to basal values of infected animals when ELISPOT is used for determination of response levels. The ratio with respect to basal response is 4-8 fold for PPD and 8 to 14 fold for Ag85B. The liposome formulation based vaccine is also able to induce a polyantigenic humoral response, which has a protective effect specially when there is a high dissemination of the infection (Guirado et al., 2006, Microbes Infect. 8, 1252-1259).

A comparison was specifically made between the data of immunogenic potency obtained with the formulation with no sucrose versus the formulation which contains sucrose as major excipient. The results obtained clearly indicate that the cellular immune response elicited by a 50 μg FCMtb dose of the formulation with sucrose is approximately 1.5-fold higher than that obtained with an identical dose of the formulation without sucrose in a single vaccination model. These higher levels of cellular immune response are obtained in both potency tests: the one conducted for batch release specifications (a single vaccination model) and the additional test included for comparability exercise (model vaccinated twice). Moreover, in both potency tests, the cellular immune response elicited by 50 μg FCMtb dose of the formulation with sucrose shows similar levels to those obtained with the 200 μg FCMtb of the sucrose-free formulation. Results, measured after reconstitution of the lyophilized liposome composition are given in FIGS. 10a and 10b. The sucrose-comprising formulation shows a significant reduction of liposomal aggregation. This is believed to be the reason for the increase in immunogenicity. The cellular immune response achieved with a 50 µg dose of the new formulation is almost comparable to that seen with a 200 µg dose obtained with the sucrose-free formulation. It is known in the field that the cellular response is considered to be the relevant response (North R J, Jung Y J (2004). Annu. Rev. Immunol. 22: 599-623).

Example 11: Manufacturing Process of the Lyophilized Liposome Formulation

One embodiment of the manufacturing process of a pharmaceutical composition comprising the liposome formulation according to the present invention is shown in FIG. 11. Briefly, it comprises the following steps 1 to 5.

(1) Preparation of the LCS bulk components

LCS bulk soy lecithin is dissolved in ethanol (1:1; w/w) and sodium cholate is dissolved in water (1:5; w/w). The solutions are sterilized by filtration. After mixing of sodium lecithin solution and sodium cholate solution, lyophilised FCMtb (Example 1) is added upon stirring. The ratios of the components are 0.03:0.2:0.7 (FCMtb:sodium cholate:soy lecithin; w/w/w).

(2) LCS bulk preparation

The aqueous phase of is transferred to a sterilised stainless steel mixer. The lipid phase of (1), containing soy lecithin, sodium cholate, and FCMtb, is added in a ratio 0.7:0.3 (aqueous phase:lipid phase, w/w). The phases are mixed at 2200 rads/s for 3 min for homogenisation and liposome formation. After homogenisation, the bulk LCS is transferred to another vessel and allowed to stand for at least 5 minutes. An IPC on particle size is performed on the LCS bulk.

(3) Dilution of LCS bulk, final formulation of liposome suspension

A 10% (w/w) solution of sucrose is prepared and sterilized. The sucrose solution is mixed with water and LCS bulk in the adequate proportions to get the final liposome suspension (LS) bulk constituted of 21 mg LCS/ml in 5% sucrose solution. pH, sterility, and particle size are tested as in-process controls.

(4) Filling

Vials are filled with 0.4 ml of LS (under continuous agitation) and partially closed for freezing and lyophilisation.

(5) Lyophilisation, packaging, and labelling

Vials are frozen at −80° C.±5° C. until lyophilisation proceeds. The lyophilisation process is performed in the range of −45° C. to 25° C. temperature and 0.150 mbars. The process lasts for 24 hours. At the end of lyophilisation vials are fully stoppered in $N_2$ atmosphere, encapsulated, labelled and stored at 5° C.±3° C.

Example 12: Adjunctive Therapy Against LTBI Will Require Only a Single Shot of 25 µg of FCMtb A Phase II double blind randomized clinical trial was set to evaluate 3 doses of FCMtb (5, 25, 50 µg, each prepared as described in the preferred mode of carrying out this invention) and placebo in 96 HIV positive (HIV+) and HIV negative (HIV−) subjects with latent tuberculosis infection (LTBI) (TST+ and Quantiferon+) that were randomly allocated in groups of n=12 per arm after receiving 1 month treatment of isoniazid. Subjects were inoculated twice with FCMtb (5, 25, 50 µg, each prepared as described in the preferred mode of carrying out this invention), immediately following isoniazid chemotherapy and 4 weeks apart.

Immunological Profile:

FCMtb (5, 25, 50 µg, each prepared as described in the preferred mode of carrying out this invention) elicited a bell-shaped, poly-antigenic response against secreted (ESAT-6, Ag85B) and structural (16 kDa, 38 kDa) antigens that were stimulated in all the doses (FIGS. 12 and 13). FCMtb (5, 25, 50 µg, each prepared as described in the preferred mode of carrying out this invention) elicited also a long term memory response (the WHO test) at the higher doses, compatible with a prophylactic effect. Surprisingly, although globally immune responses were more intense in HIV− than in HIV+, the single inoculation of 25 µg of FCMtb (5, 25, 50 µg, each prepared as described in the preferred mode of carrying out this invention) elicited the best immune response in both populations (FIGS. 12 and 13).

Conclusion:

A single inoculation of 25 µg is the best choice for adjunctive therapy against LTBI in HIV negative and HIV positive subjects.

Figure 1:
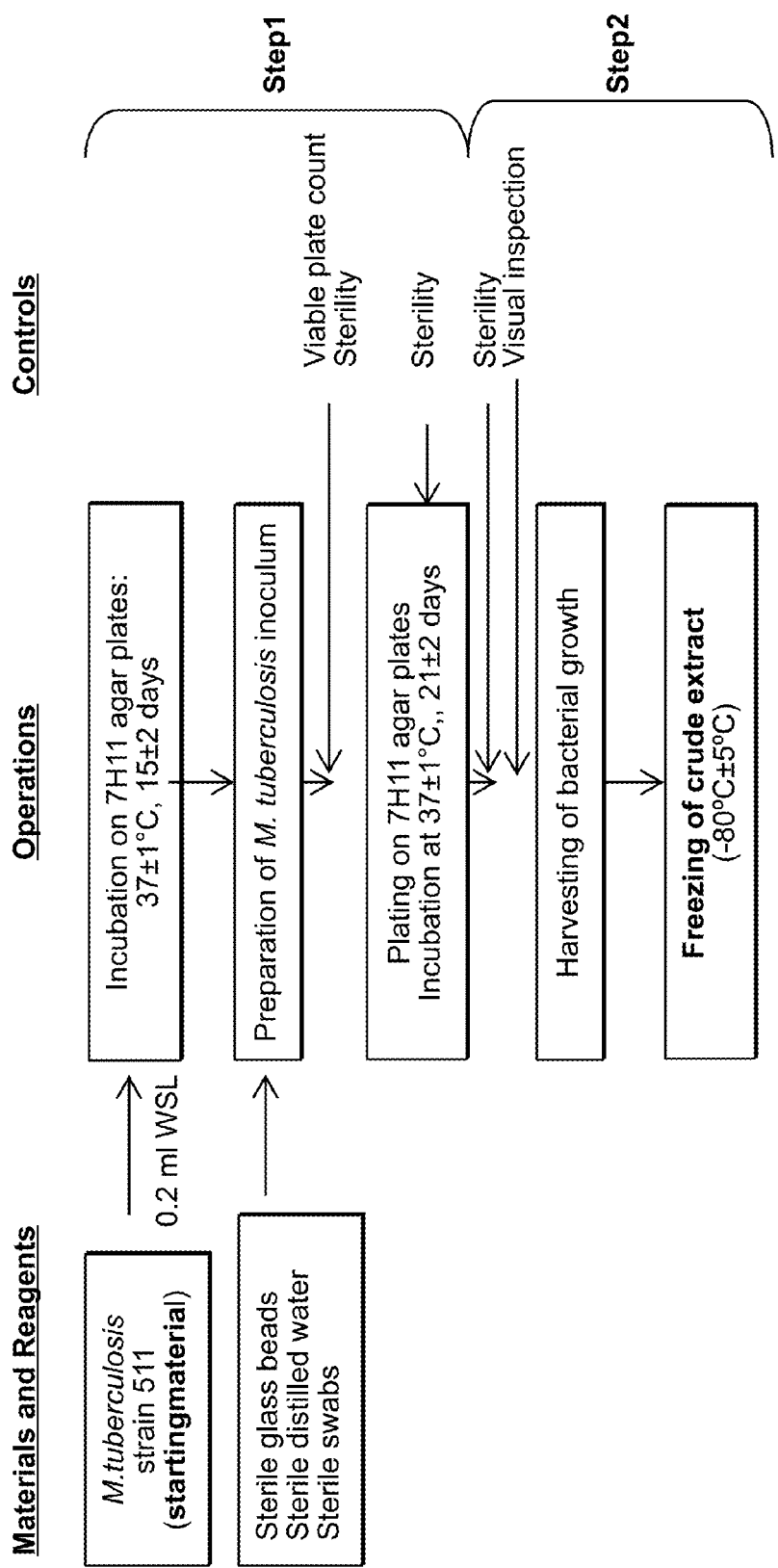
FIG. 1: Flow-chart showing upstream process of the drug substance FCMtb, including the materials and reagents involved in the process and suitable in-process controls.
Figure 2:
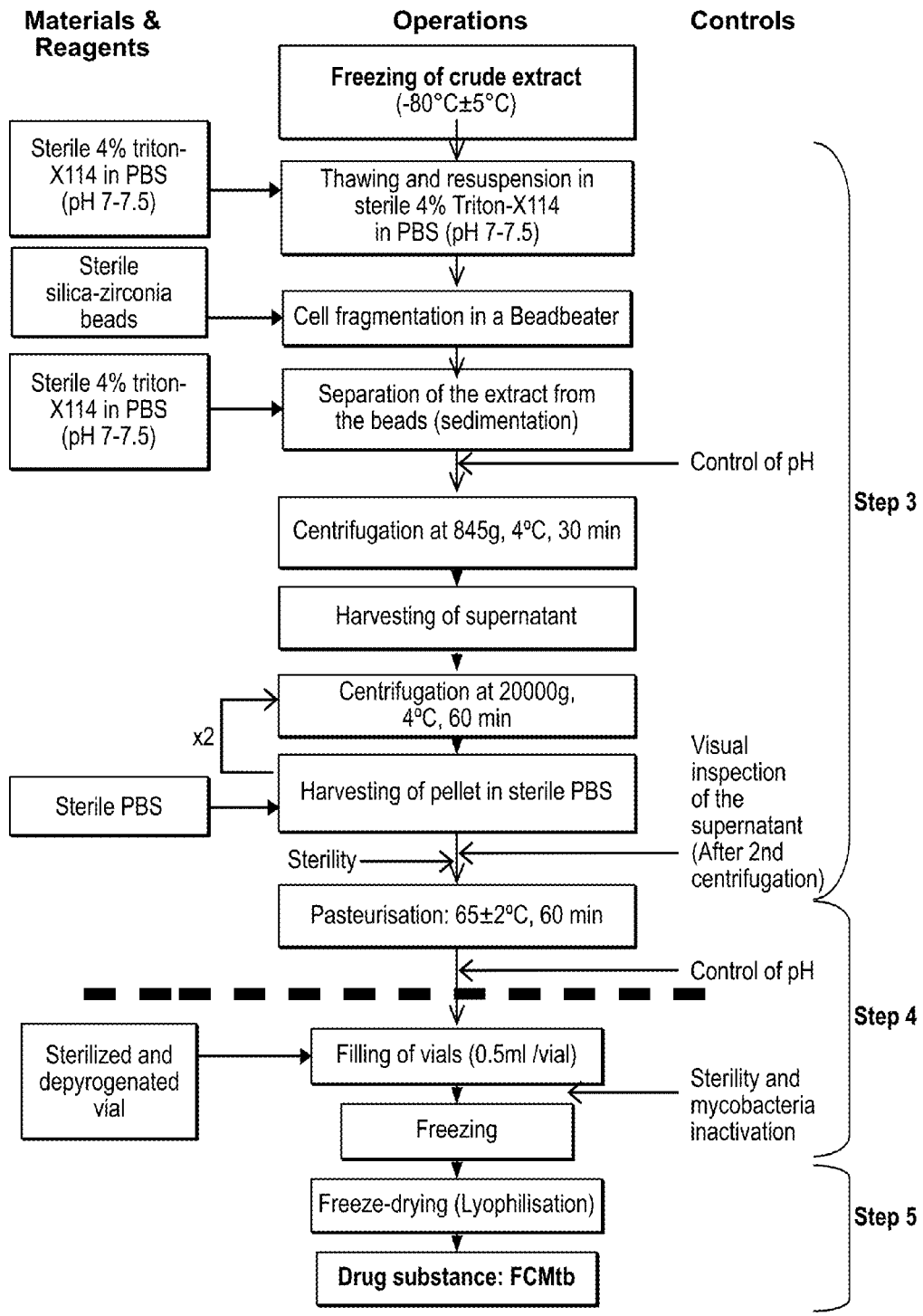
FIG. 2: Flow-chart showing downstream process of the drug substance FCMtb, including the materials and reagents involved in the process and suitable in-process controls.
Figure 3:
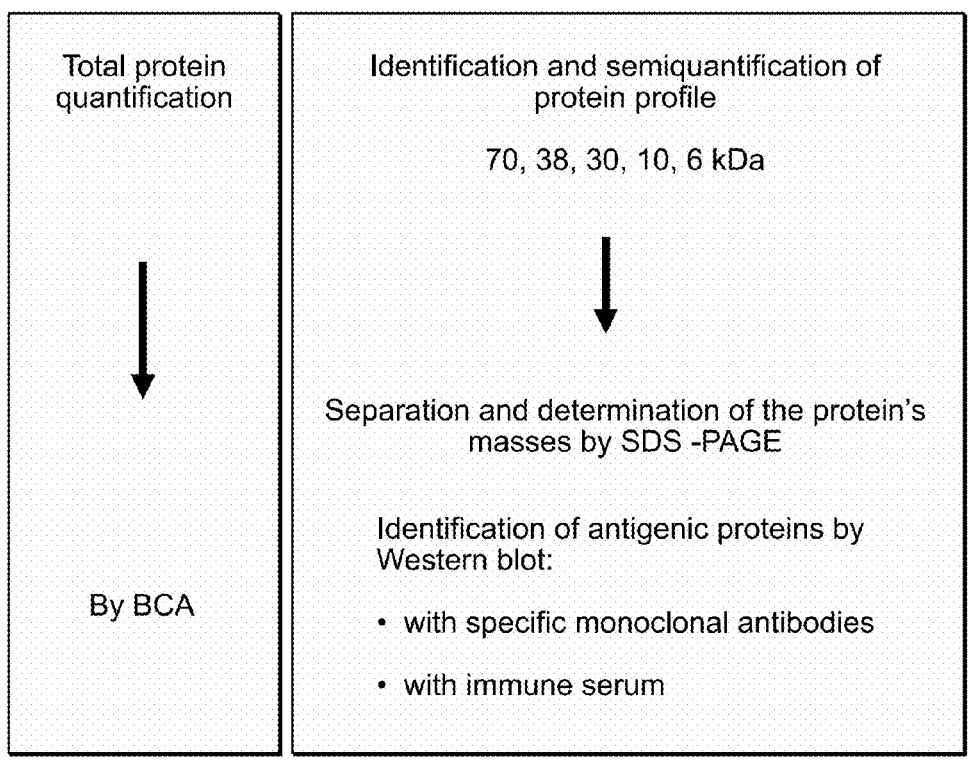
FIG. 3: Flow-chart of protein characterization.
Figure 4:
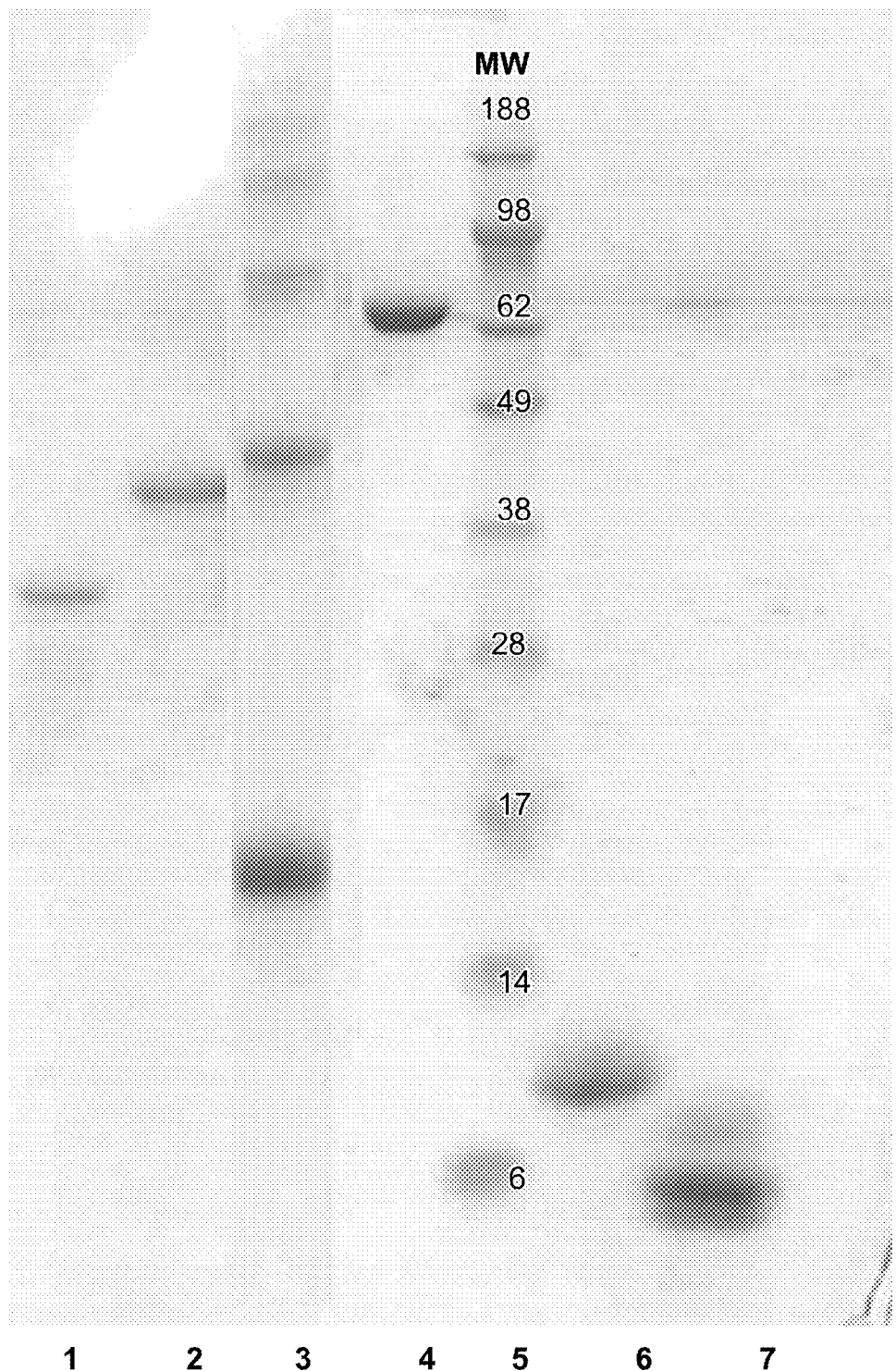
FIG. 4: Identification of antigens by SDS-PAGE and Coomassie Blue Stain methodology. Reference antigens ESAT6 (6 kDa) (7); CFP10 (10 kDa) (6); Ag85B (30 kDa) (1); 38 kDa (2); lipopolypeptide (19 kDa) (3); HSP70 (70 kDa) (4); as well as Molecular Weight marker MW (5), are shown.
Figures 5A, 5B:
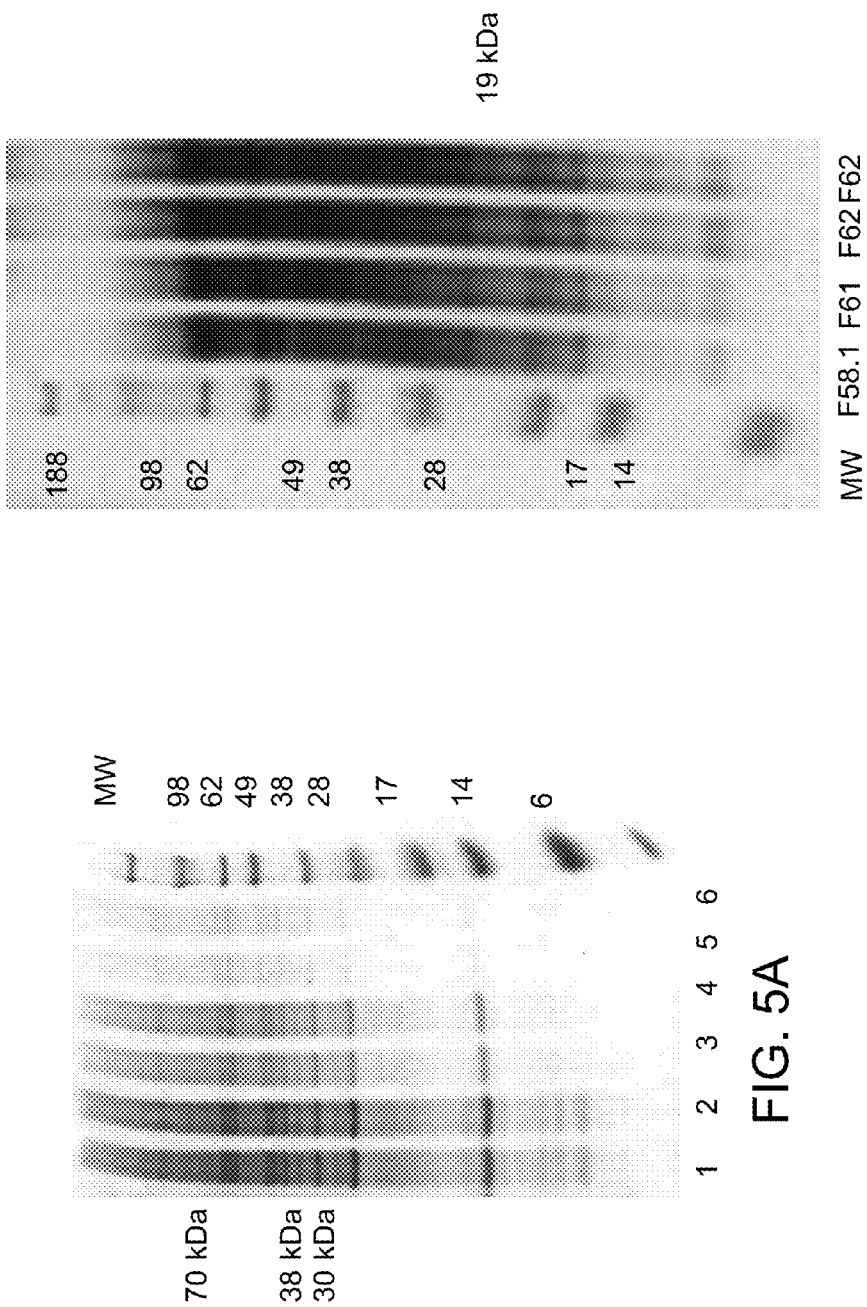
FIG. 5a: Protein profile: Protein profile of reference standard FCMtb-52.1 (1 to 6) at final concentrations of 15.6 µg FCMtb/mL (1, 2), 6.25 µg FCMtb/mL (3, 4) and 1.56 µg FCMtb/mL (5, 6), SDS page followed by Coomassie stain. MW in kDa. 5b: Identification of the 19 kDa band, SDS page followed by silver staining. 5c: Protein profile: Identification of bands (10 kDa and 6 kDa) in the indicated FCMtb batches by SDS-PAGE and Silver Stain methodology carried out in parallel with ESAT-6 standard from Lionex. Different FCMtb batches (1, 2, 3, 9, 10, 11, (batch FCMtb-52.1 in lane 9)), ESAT-6 standard from Lionex at different concentrations (4 to 8); 5d: Western Blot Identification of antigen M. tuberculosis HSP70 (Rv 0350) in FCMtb batches by Western-blot using specific antibodies parallel to M. tuberculosis HSP70 standard. Different FCMtb batches (1, 2, 3, 4, 7, 8, 9), HSP70 standard (5, 6); 5e: Identification of antigen M. tuberculosis 38 kDa (Rv 0934) in FCMtb batches by Western-blot methodology using a specific antibody and carried out in parallel with M. tuberculosis 38 kDa standard from Lionex. Fluorescence detection using the Odyssey System. Different FCMtb batches (1, 2, 3, 6, 7), 38 kDa standard (4, 5). 5f: Identification of antigen Ag85B (Rv 1886c) in FCMtb batches by Western-blot methodology using a specific antibody and carried in parallel with M. tuberculosis Ag85B standard from Lionex. Fluorescence detection using the Odyssey System. FCMtb batches (1, 2, 3, 5, 6, 7), Ag85B standard (4).
Figure 5C:
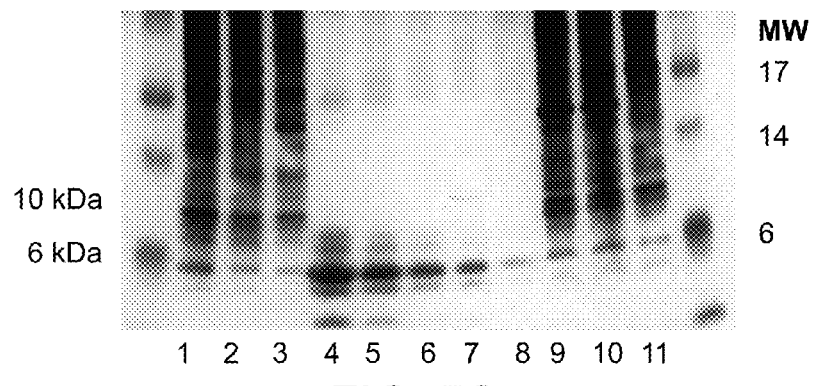
FIG. 5: Protein characterisation.
Figure 5D:
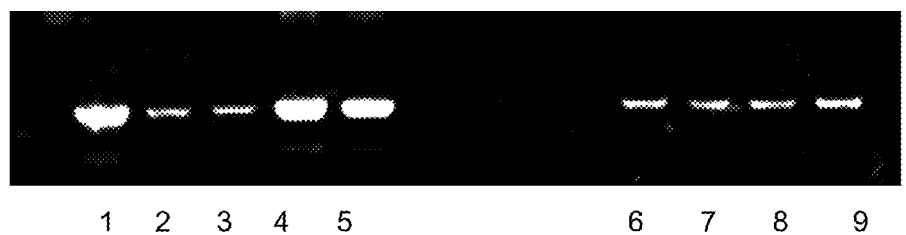
Figure 5E:
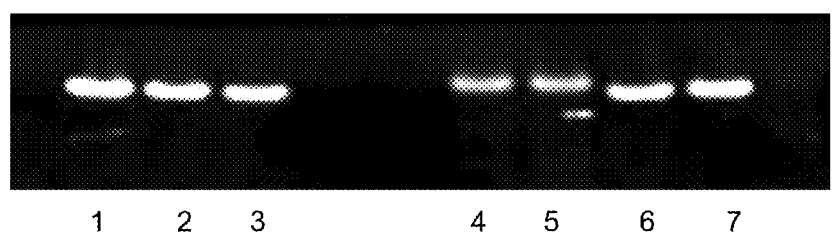
Figure 5F:
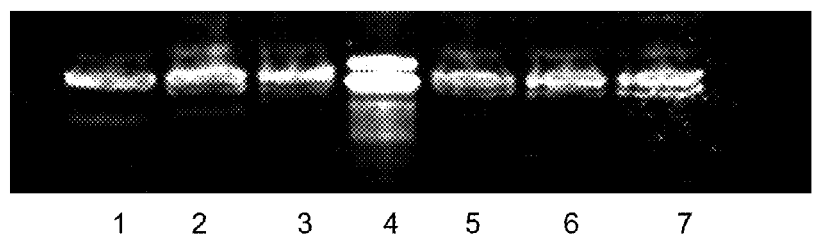
Figure 6:
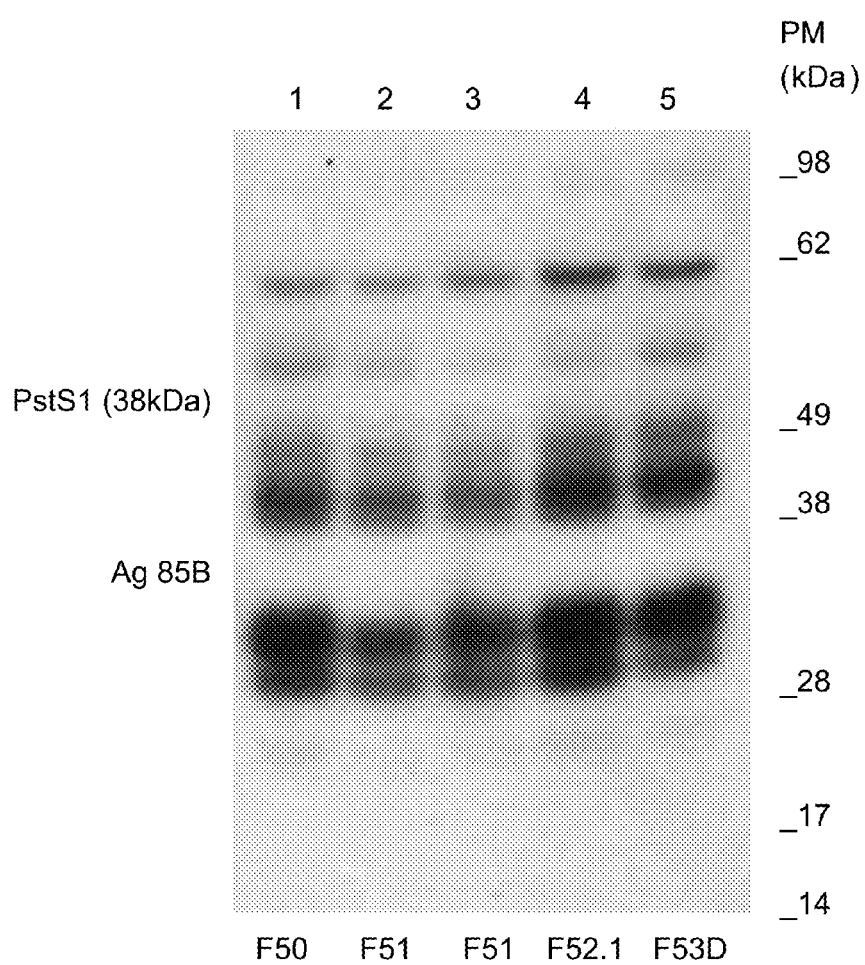
FIG. 6: Interaction of indicated protein bands of different FCMtb batches (50 μg/lane) with 1/8000 diluted serum obtained from infected mice after being inoculated twice with the liposome formulation based pharmaceutic vaccine composition according to this invention, using Western-blot methodology.
Figure 7A:
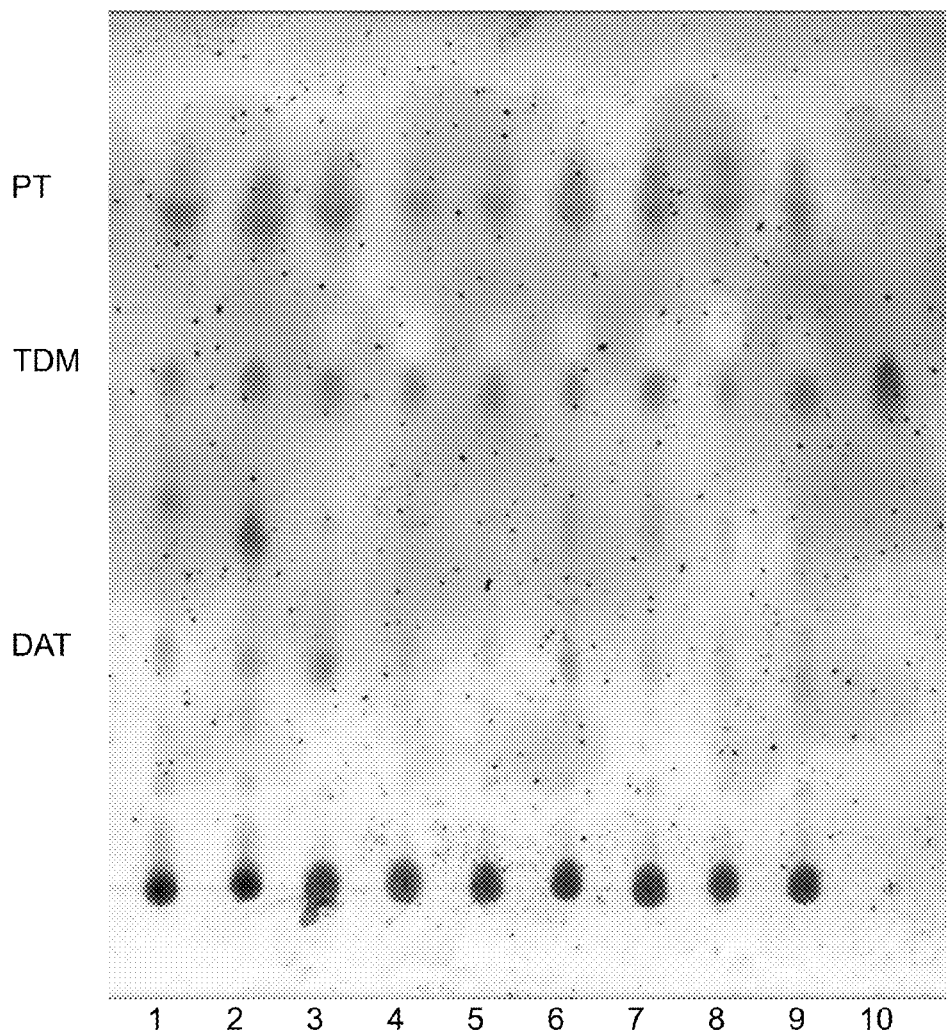
FIG. 7: Lipid analysis. 7a: Identification of polyacyltrehalose (PT), trehalose 6,6'-dimycolate (TDM) and diacyltrehalose (DAT) in reference strains (H37Rv (2) and NCTC 13536 (1) and different FCMtb batches (3-9), and TDM standard (10) by TLC methodology. 7b: Identification of trehalose 6,6'-dimycolate (TDM) in FCMtb batches by TLC methodology. Panels (A) and (B) represent two independent assays. (A) TDM standard (11) and (12), other lanes different FCMtb batches. B: (1) TDM standard (1), other lanes different FCMtb batches. 7c: Pattern of mycolic acids I, III and IV in FCMtb batches by TLC methodology. Panels (A), (B) and (C) represent three independent assays. (A) FCMtb batches (1-6 (FCMtb-51.2 standard 6)). (B) for illustration/reference, (C) batch FCMtb-47b (1) compared with mycolic acid standard (2). 7d: Identification of LAM (reference in left lane, samples derived from liposomes according to the invention in remaining lanes).
Figure 7B:
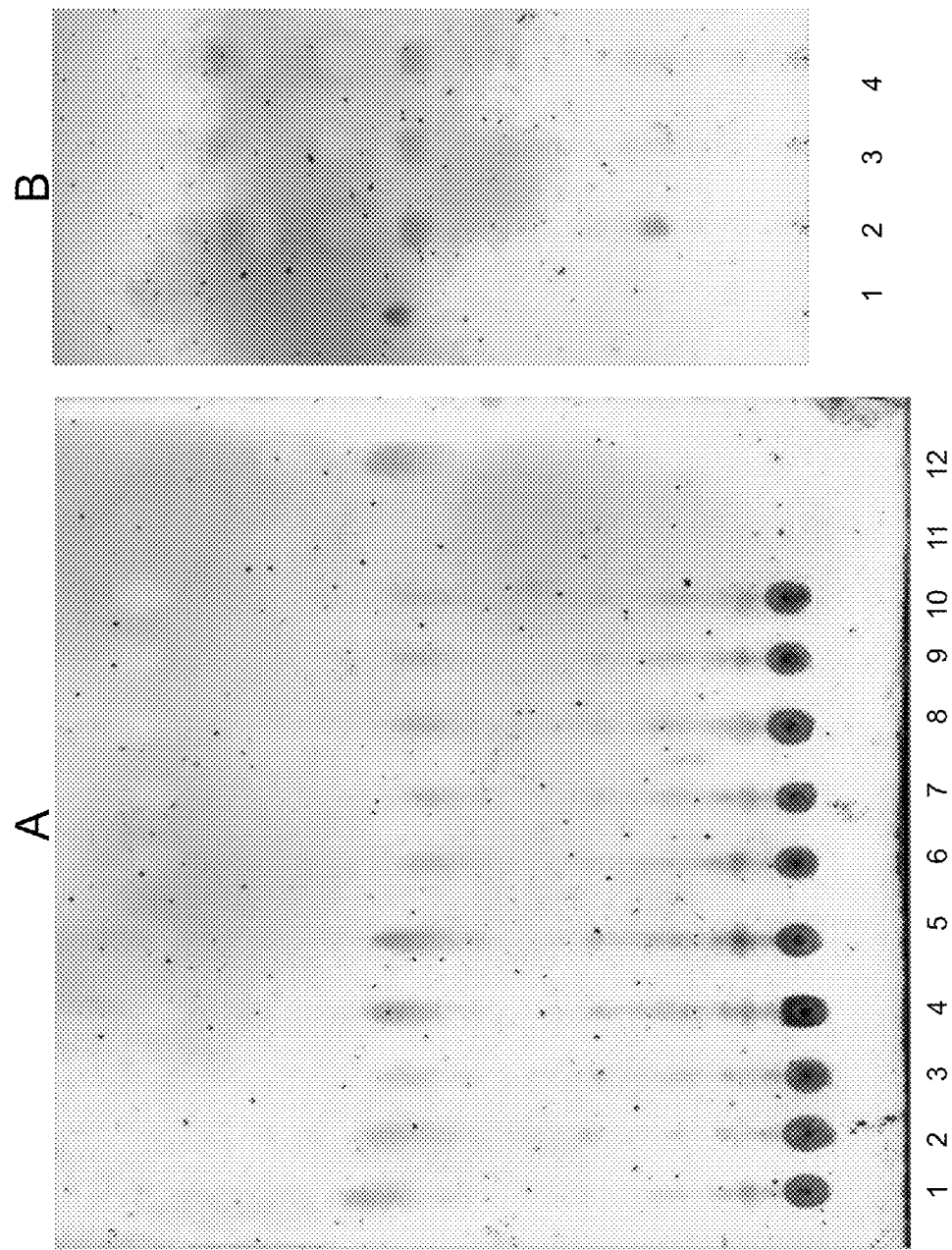
Figure 7C:
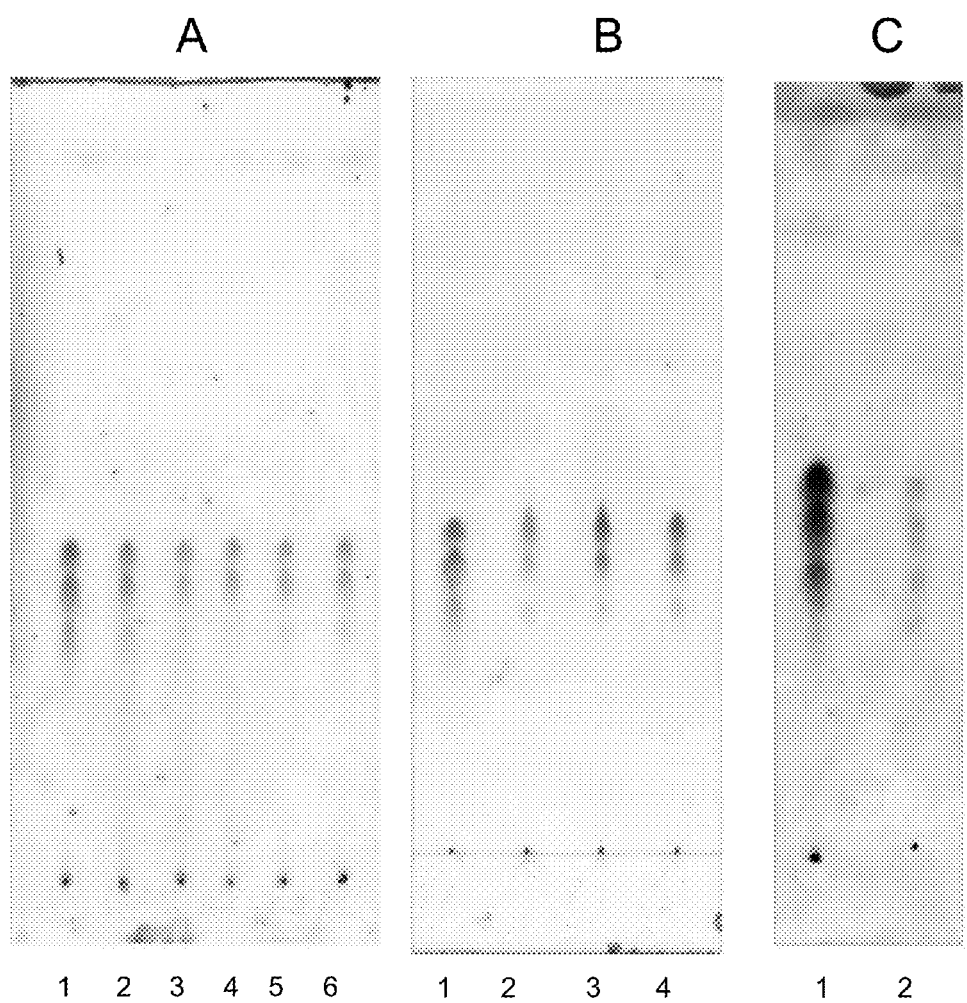
Figure 7D:
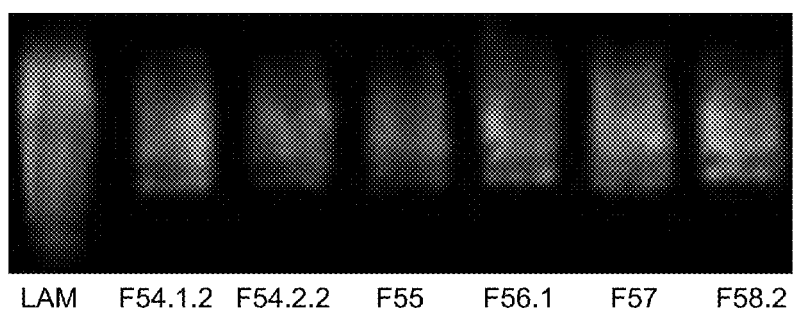
Figure 8:
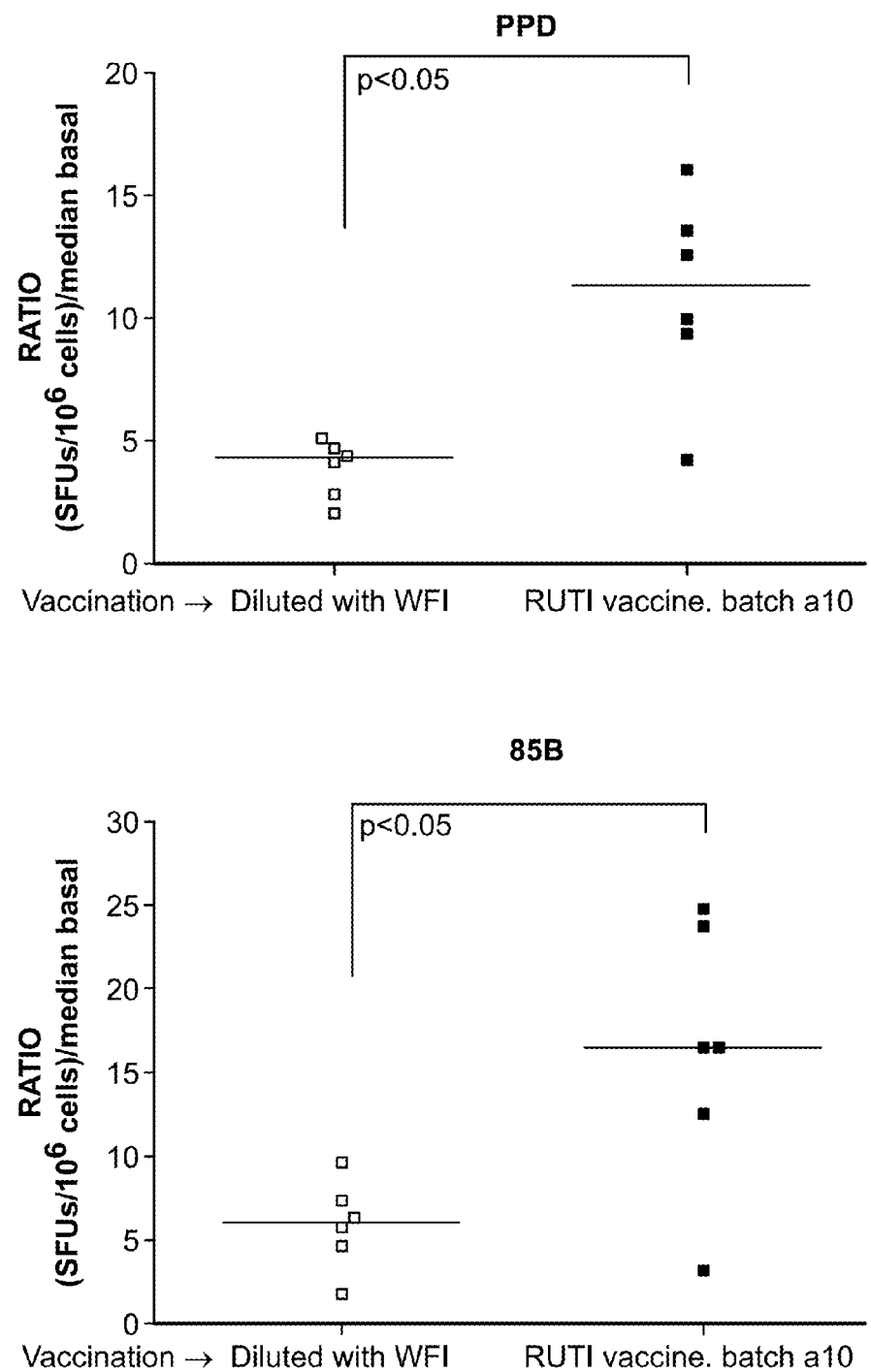
FIG. 8: Comparison of cellular immunopotency of FCMtb resuspended with water for injection (WFI) versus FCMtb formulated with liposomes (labelled RUTI vaccine, batch 10a), at the same dose (50 μg/dose).
Figure 9:
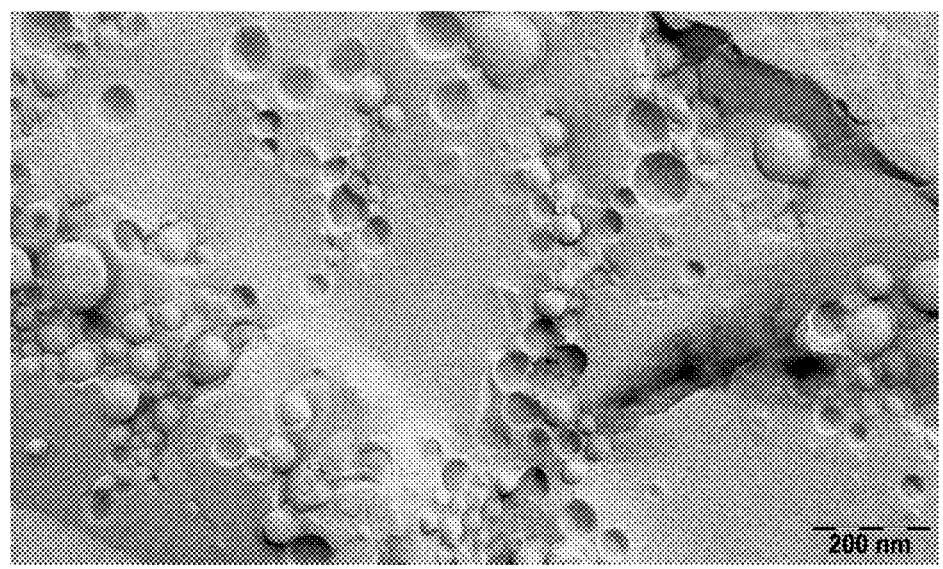
FIG. 9: Freeze-fracturing preparation of liposomal concentrate (LCS) bulk (electronic microscopy).
Figure 10A:
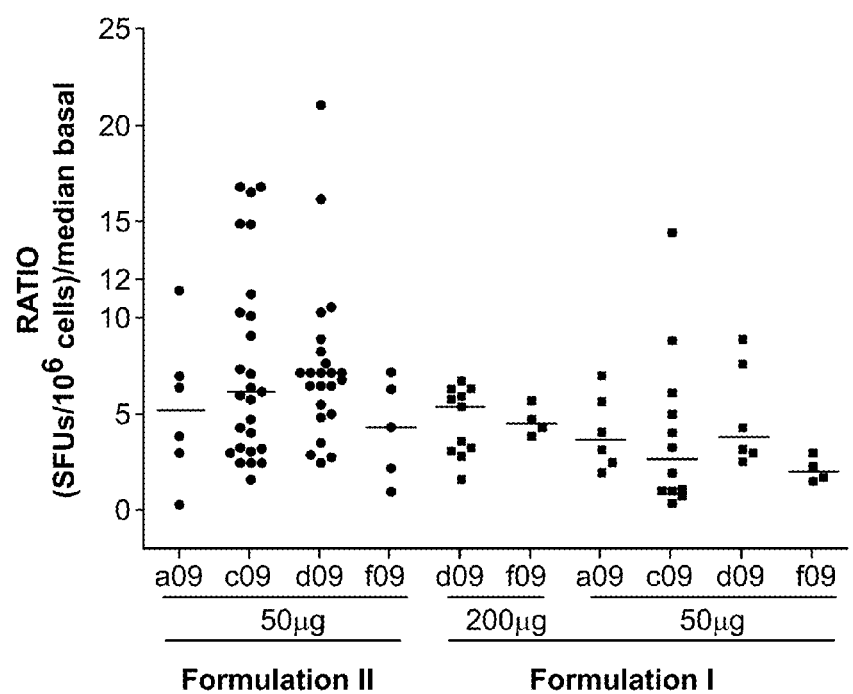
FIG. 10: a: Cellular immune response per batch tested with the two formulations of vaccine in a potency test (one vaccination). b: as in a, but two vaccinations. "Formulation II": comprising 5% (w/w) sucrose, according to Table 1 of this document. "Formulation I": as formulation II, except that no sucrose is present. μg refers to μg FCMtb/dose. 85B: Ag85B.
Figure 10A:
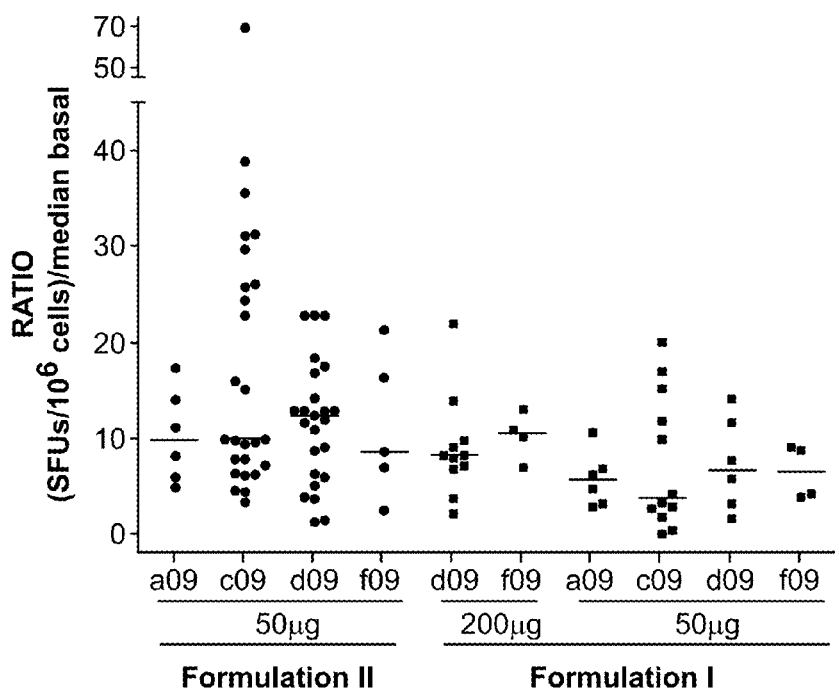
Figure 10B:
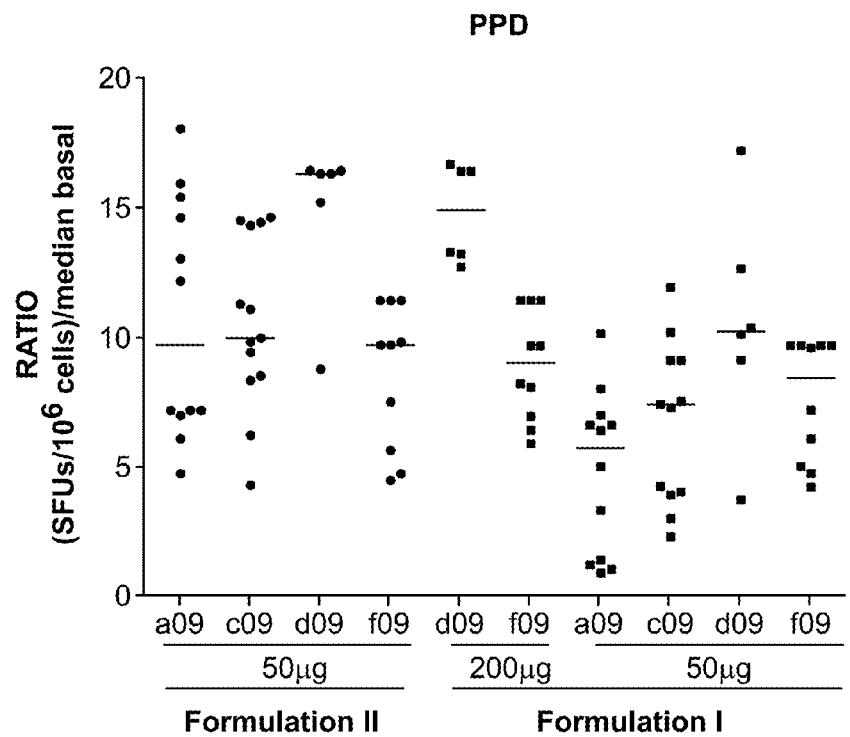
Figure 10B:
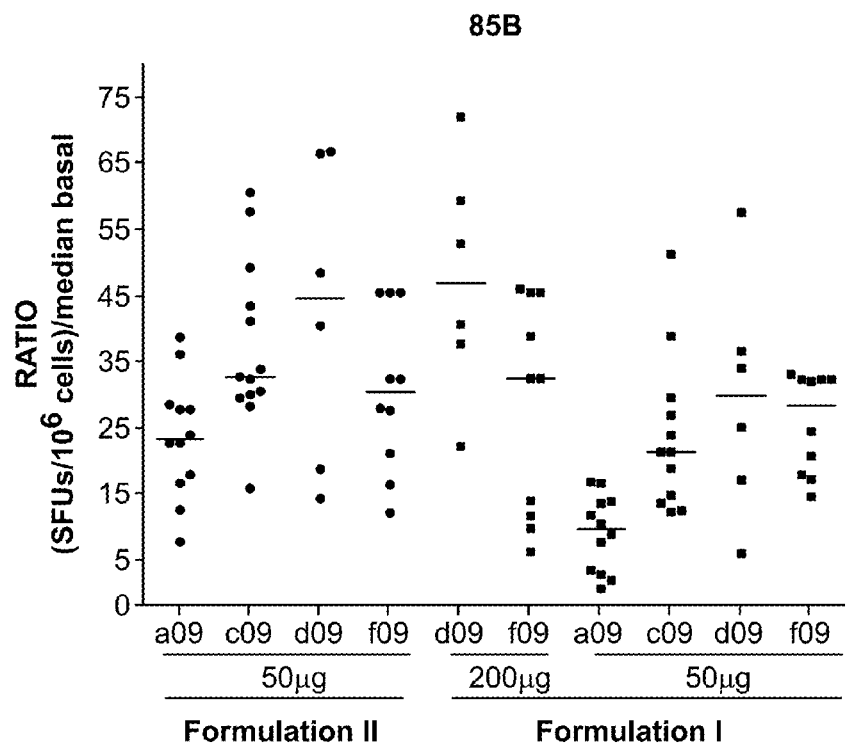
Figure 11:
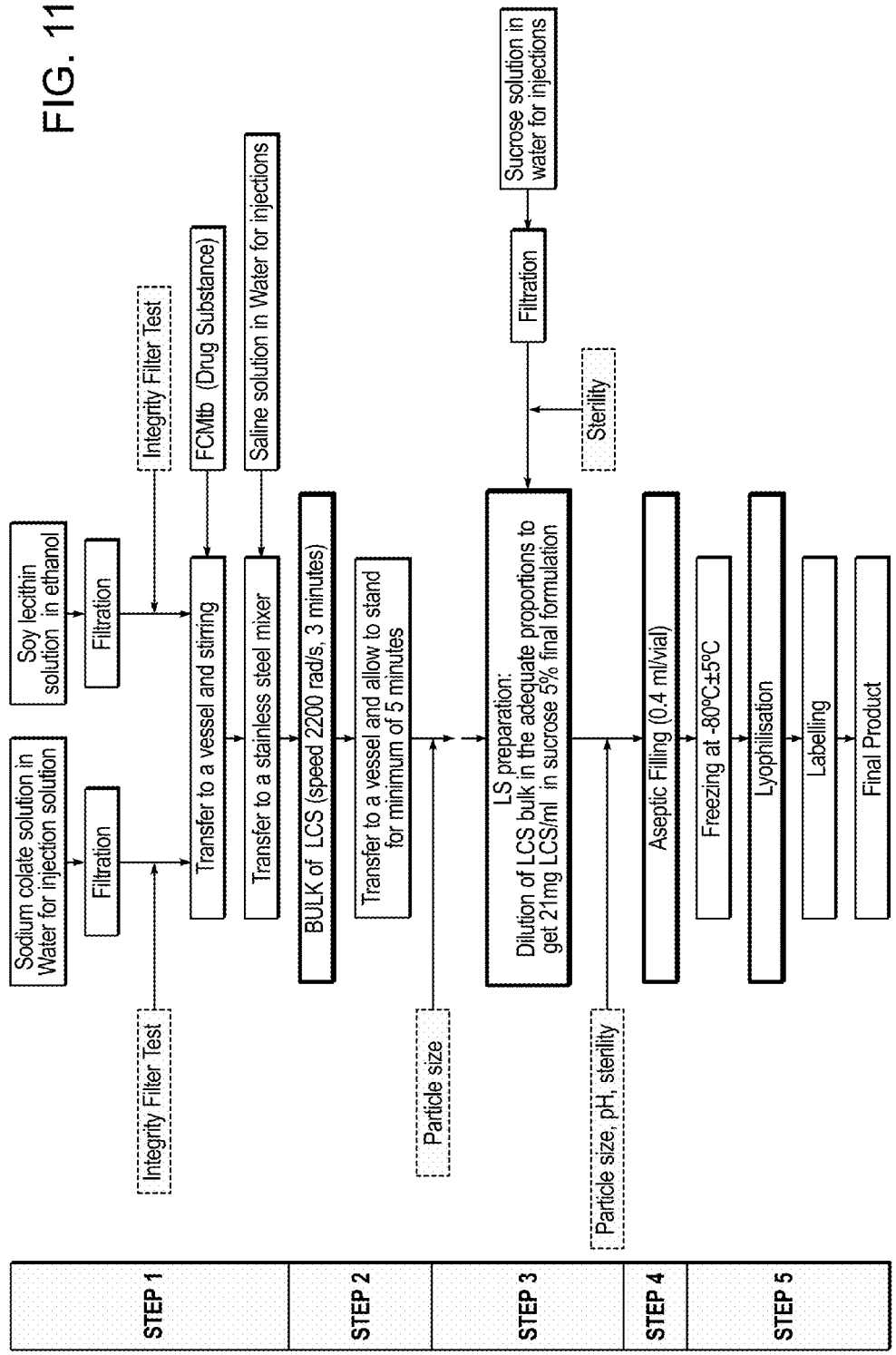
FIG. 11: Flow-chart of the process according to the preferred mode of carrying out this invention.
Figure 12:
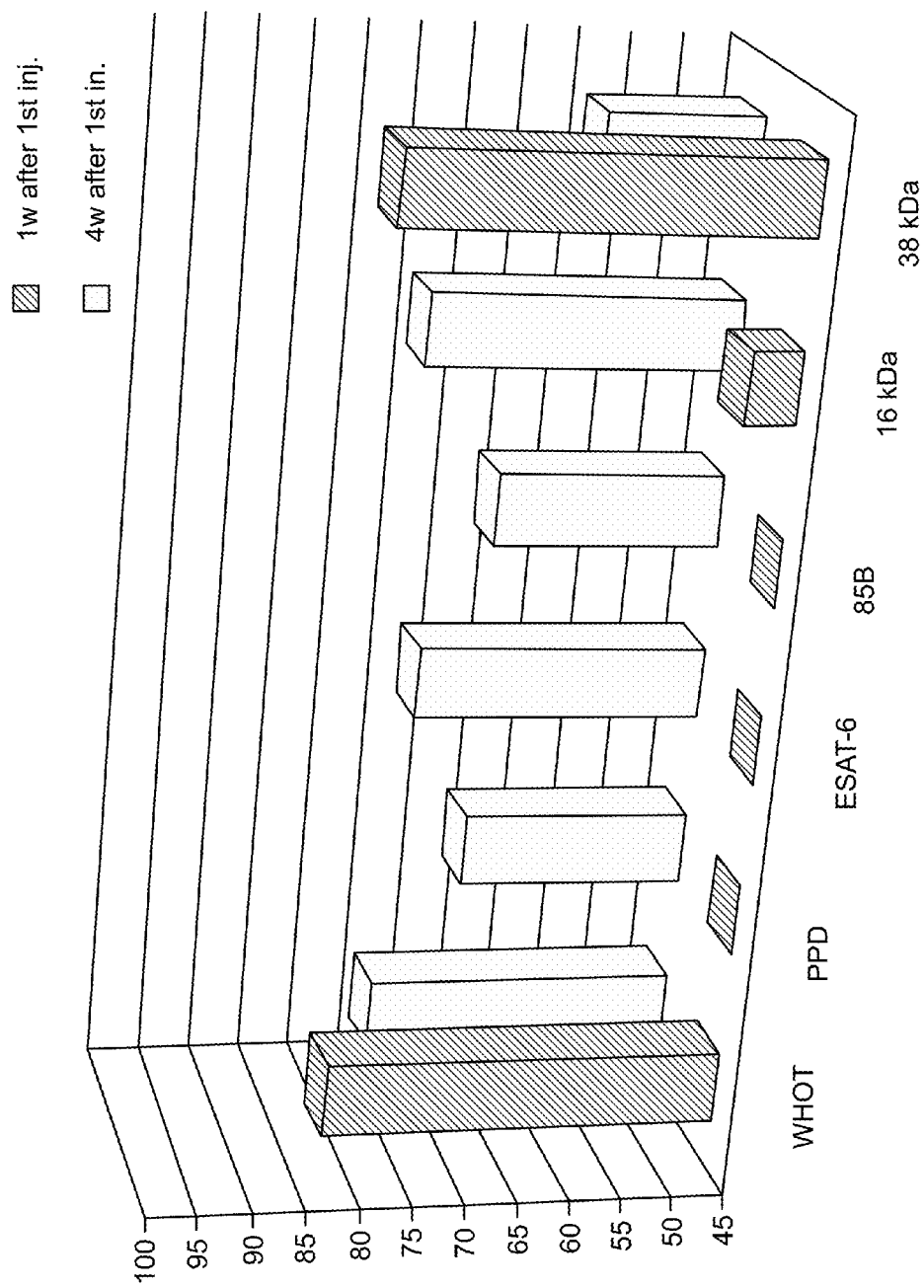
FIG. 12: Immunological profile of 1 inocculation of RUTI 25 μg as described in Example 12.
Figure 13:
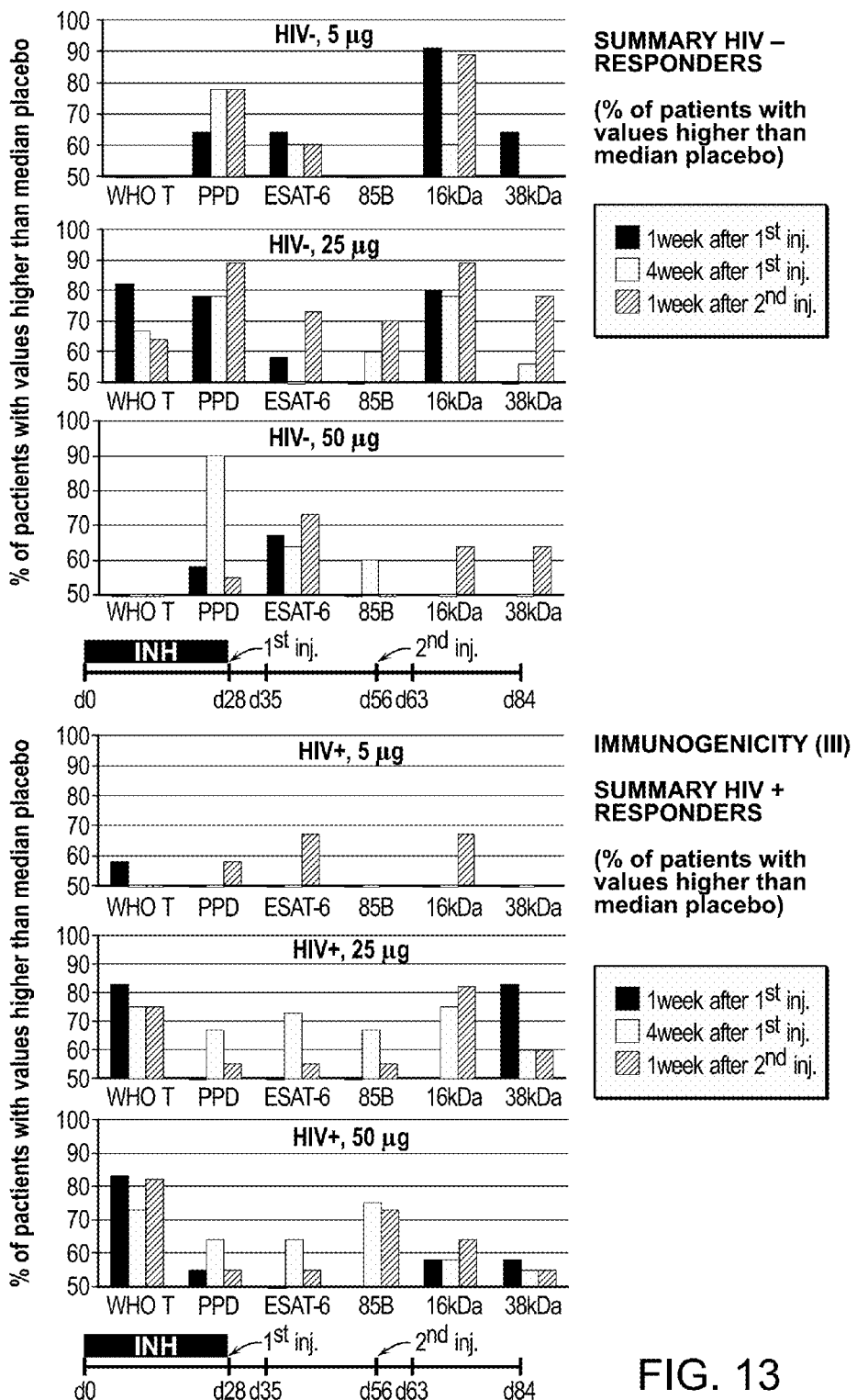
FIG. 13: Immunogenicity (HIV− and HIV+) as described in Example 12.

The invention claimed is:

1. A liposome formulation comprising:
   (a) fragments from a *Mycobacterium tuberculosis*-complex (MTB-C) strain (FCMtb), wherein said fragments are capable of inducing an immune response,
   (b) a liposome forming agent,
   (c) 1 to 20% (w/v) sucrose;
   wherein the liposome formulation has a z-average particle size of 120 nm or less.

2. The liposome formulation according to claim 1, wherein the z-average particle size is in the range from 40 to 110 nm.

3. The liposome formulation according to claim 1, wherein the liposome formulation is an emulsion.

4. The liposome formulation according to claim 1, wherein a particle polydispersity index is 0.4 or less.

5. The liposome formulation according to claim 1, wherein the *Mycobacterium tuberculosis*-complex (MTB-C) strain is a virulent *Mycobacterium tuberculosis*-complex (MTB-C) strain.

6. The liposome formulation according to claim 1, additionally comprising (d) a tensioactive agent
   and/or
   (e) one or more non-ionic surfactants.

7. The liposome formulation according to claim 1, wherein the fragments from a *Mycobacterium tuberculosis*-complex (MTB-C) strain (FCMtb) are or comprise cell wall fragments.

8. The liposome formulation according to claim 6, wherein the ratio between (a) and (d) is between 0.05:1 and 1:5 (w/w).

9. The liposome formulation according to claim 1, wherein the liposome forming agent is a hydrogenated, partially hydrogenated or non-hydrogenated phospholipid.

10. The liposome formulation according to claim 6, wherein the tensioactive agent is selected from cholate, deoxycholate, cholesterol and cholesterol hemisuccinate.

11. The liposome formulation according to claim 1, comprising fragments of the MTB-C strain NCTC 13536, deposited in 2010 at the NCTC in London.

12. The liposome formulation according to claim 1, wherein the fragments from a *Mycobacterium tuberculosis*-complex (MTB-C) strain (FCMtb) are capable of inducing an immune response and comprise at least two of the following polypeptides:
   (i) a first polypeptide having a molecular weight of about 70 kDa as measured following electrophoresis on a sodium dodecylsulfate (SDS) polyacrylamide gel,
   (ii) a second polypeptide having a molecular weight of about 38 kDa as measured following electrophoresis on a sodium dodecylsulfate (SDS) polyacrylamide gel,
   (iii) a third polypeptide having a molecular weight of about 30 kDa as measured following electrophoresis on a sodium dodecylsulfate (SDS) polyacrylamide gel,
   (iv) a fourth polypeptide having a molecular weight of about 10 kDa as measured following electrophoresis on a sodium dodecylsulfate (SDS) polyacrylamide gel, and
   (i) a fifth polypeptide having a molecular weight of about 6 kDa as measured following electrophoresis on a sodium dodecylsulfate (SDS) polyacrylamide gel.

13. The liposome formulation according to claim 1, wherein the fragments from a *Mycobacterium tuberculosis*-complex (MTB-C) strain (FCMtb) are capable of inducing an immune response and comprise at least one of the following polypeptides: HSP70, 38 kDa protein and Ag85B.

14. The liposome formulation according to claim 1, comprising one or more mycolic acids and/or a sugar-conjugated mycolate.

15. The liposome formulation according to claim 1, additionally comprising one or more non-ionic surfactants.

16. The liposome formulation according to claim 1, additionally containing one or more salts or a solution thereof.

17. The liposome formulation according to claim 1, wherein the liposome formulation is freeze-dried.

18. A suspension comprising the liposome formulation according claim 17, wherein the liposome formulation is reconstituted in a solvent.

19. A pharmaceutical composition comprising
   the liposome formulation according to claim 1 or
   a suspension comprising said liposome formulation, wherein the liposome formulation has been freeze-dried and subsequently reconstituted in a solvent,
   and a pharmaceutically acceptable carrier or diluent, and/or a pharmaceutically acceptable adjuvant.

20. A method of treating or preventing tuberculosis in a human subject in need thereof, the method comprising:

administering to said human subject:

the liposome formulation of claim 1; or a suspension comprising said liposome formulation;

wherein said liposome formulation has been freeze-dried and subsequently reconstituted in a solvent, wherein the solvent is preferably aqueous, and more preferably is or comprises physiological serum; or a pharmaceutical composition comprising said liposome formulation or said suspension and a pharmaceutically acceptable carrier or diluent, and/or a pharmaceutically acceptable adjuvant.

21. The method according to claim 20, wherein said human subject:

(a) is suffering from latent tuberculosis and is at risk of developing active tuberculosis;

(b) had been exposed to tuberculosis, but is not yet infected; or (c) is at risk of developing latent tuberculosis.

22. The method according to claim 20, wherein the liposome formulation, the suspension or the pharmaceutical composition is administered to the human body in a dose comprising 1 to 1000 μg/dose FCMtb.

23. The method according to claim 20, wherein the liposome formulation, the suspension or the pharmaceutical composition is administered to the human body in a single inoculation dose of 25 pg FCMtb.

24. The method according to claim 20, wherein the liposome formulation, the suspension or the pharmaceutical composition is administered to the human body as a part of a combination therapy.

25. The method according to claim 23, wherein the liposome formulation, the suspension or the pharmaceutical composition is administered in adjunctive therapy.

26. The method according to claim 25, wherein the liposome formulation, the suspension or the pharmaceutical composition is administered as a part of adjunctive therapy to an HIV positive human subject.

27. The method according to claim 23, wherein the liposome formulation, the suspension or the pharmaceutical composition is administered to an HIV negative human subject.

* * * * *